(12) United States Patent
Wu et al.

(10) Patent No.: US 9,168,113 B2
(45) Date of Patent: *Oct. 27, 2015

(54) TOOTH MOVEMENT MEASUREMENT BY AUTOMATIC IMPRESSION MATCHING

(71) Applicant: Align Technology, Inc., San Jose, CA (US)

(72) Inventors: Fuming Wu, Pleasanton, CA (US); Vadim Matov, San Jose, CA (US); Jihua Cheng, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/089,658

(22) Filed: Nov. 25, 2013

(65) Prior Publication Data

US 2014/0087324 A1   Mar. 27, 2014

Related U.S. Application Data

(63) Continuation of application No. 12/334,329, filed on Dec. 12, 2008, now Pat. No. 8,591,225.

(51) Int. Cl.
*A61C 7/00* (2006.01)
*A61C 9/00* (2006.01)
*A61C 7/08* (2006.01)

(52) U.S. Cl.
CPC ............ *A61C 9/0053* (2013.01); *A61C 7/00* (2013.01); *A61C 7/002* (2013.01); *A61C 7/08* (2013.01); *A61C 9/0006* (2013.01)

(58) Field of Classification Search
CPC ............ A61C 7/00; A61C 7/002; A61C 7/08; A61C 9/0006; A61C 9/0053

USPC ......................................................... 382/128
See application file for complete search history.

(56) References Cited

U.S. PATENT DOCUMENTS

| | | | |
|---|---|---|---|
| 2,467,432 | A | 4/1949 | Kesling |
| 3,407,500 | A | 10/1968 | Kesling |
| 3,600,808 | A | 8/1971 | Reeve |
| 3,660,900 | A | 5/1972 | Andrews |
| 3,683,502 | A | 8/1972 | Wallshein |
| 3,738,005 | A | 6/1973 | Cohen |
| 3,860,803 | A | 1/1975 | Levine |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los ngeles, CA, p. 195.

(Continued)

*Primary Examiner* — Edward Moran
(74) *Attorney, Agent, or Firm* — Wilson Sonsini Goodrich & Rosati

(57) ABSTRACT

The present invention relates to systems and methods for detecting deviations from an orthodontic treatment plan. One method includes receiving a tracking model, performing a matching step between individual teeth in a plan model and the tracking model, comparing the tracking model with the plan model, and detecting one or more positional differences.

23 Claims, 28 Drawing Sheets

(56) References Cited

U.S. PATENT DOCUMENTS

| | | |
|---|---|---|
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 8,591,225 B2 | 11/2013 | Wu et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |
| 2005/0048432 A1 | 3/2005 | Choi et al. |
| 2005/0055118 A1 | 3/2005 | Nikolskiy et al. |

(56) References Cited

U.S. PATENT DOCUMENTS

| | | | |
|---|---|---|---|
| 2007/0003900 A1 | 1/2007 | Miller | |
| 2008/0305451 A1 | 12/2008 | Kitching et al. | |
| 2010/0151404 A1 | 6/2010 | Wu et al. | |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et al, "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures,"AADR Abstracts, Program and Abstracts of Papers, 57th General Session, IADR HP Annual Session, Mar. 29-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging q Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty, NATO Symposium on Applications of Human Biostereometrics," Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III, Aug. 26-30, 1975, pp. 142-166.
Baumrind, "Integrated Three-Dimensional Craniofacial Mapping: Background, Principles, and Perspectives," Semin in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004,URL <http://astronomy.swin.edu.au/—pbourke/prolection/coords>.
Boyd et al., "Three Dimensional Diagnosis and Orthodontic Treatment of Complex Malocclusions With the Invisalipn Appliance," Semin Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979.
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin Orthod., 7(4):258-265 (Dec. 2001).

(56) References Cited

OTHER PUBLICATIONS

Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988.
Duret et al., "CAD/CAM Imaging in Dentistry," Curr. Opin. Dent., 1:150-154 (1991.
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979.
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987.
Friede et al., "Accuracy of Cephalometric Prediction in Orthognathic Surgery," Abstract of Papers, J. Dent. Res., 70:754-760 (1987.
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001.
Gim-Alldent Deutschland, "Das DUX System: Die Technik," 2 pages total (2002).
Gottleib et al., "JCO Interviews Dr. James A. McNamara, Jr., on the Frankel Appliance: Part 2: Clinical 1-1 Management, "J. Clin. Orthod., 16(6):390-407 (Jun. 1982.
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989.
Heaven et a/., "Computer-Based Image Analysis of Artificial Root Surface Caries, Abstracts of Papers," J. Dent. Res., 70:528 (Apr. 17-21, 1991.
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingamp-production/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total.
Hoffmann, et al., "Role of Cephalometry for Planning of Jaw Orthopedics and Jaw Surgery Procedures," 0 (Article Summary in English, article in German), lnformatbnen, pp. 375-396 (Mar. 1991.
Hojjatie et al., "Three-Dimensional Finite Element Analysis of Glass-Ceramic Dental Crowns," J. Biomech., 23(11):1157-1166 (1990.
Huckins, "CAD-CAM Generated Mandibular Model Prototype from MRI Data," AAOMS, p. 96 (1999.
Important Tip About Wearing the Red White & Blue Active Clear Retainer System, Allesee Orthodontic Appliances-Pro Lab, 1 page 1998).
Inside the ADA, JADA, 118:286-294 (Mar. 1989).
JCO Interviews, Craig Andreiko, DDS, MS on the Elan and Orthos Systems, JCO, pp. 459-468 (Aug. 1994.
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988.
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46. Jan. 1978.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, KN Am. J. Orthod. Oral Surg. (1946) 32:285-293.
Ki Kamada et.al., Case Reports on Tooth Positioners Using LTV Vinyl Silicone Rubber, J. Nihon University School of Dentistry (1984) 26(1): 11-29.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989.
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989.
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.

(56) References Cited

OTHER PUBLICATIONS

Nahoum, "The Vacuum Formed Dental Contour Appliance," N.Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and q Essix Appliances, <httpz;//www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et a/., "CAD/CAM for Dental Restorations—Some of the Curious Challenges," IEEE Trans. Biomed. Eng., 38(4):314-318 (Apr. 1991.
Rekow et al., "Comparison of Three Data Acquisition Techniques for 3-D Tooth Surface Mapping," LM Annual International Conference of the IEEE Engineering in Medicine and Biology Society, 13(1):344-345 1991.
Rekow, "A Review of the Developments in Dental CAD/CAM Systems," (contains references to LN Japanese efforts and content of the papers of particular interest to the clinician are indicated with a one line summary of their content in the bibliography), Curr. Opin. Dent., 2:25-33 (Jun. 1992.
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987.
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.

Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992.
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile!Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed on Jun. 20,1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998.
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987.
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13,1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

(56) References Cited

OTHER PUBLICATIONS

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001.

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); I11.—The General Concept of the D.P. Method and Its Therapeutic Effect, Part 2. Skeletal Reversed Occlusion Case Reports," Nippon Dental Review, 458:112-129 (Dec. 1980.

Yoshii, "Research on a New Orthodontic Appliance: The Dynamic Positioner (D.P.); I11. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances-Pro Lab product information for patients, 2 pages (2002).

TOOTH MOVEMENT MEASUREMENT BY AUTOMATIC IMPRESSION MATCHING

CROSS-REFERENCE

This application is a continuation of U.S. patent application Ser. No. 12/334,329, filed Dec. 12, 2008, now U.S. Pat. No. 8,591,225, issued Nov. 26, 2013, the contents of which is incorporated herein by reference.

This application is related to U.S. patent application Ser. No. 11/760,689, filed on Jun. 8, 2007; U.S. patent application Ser. No. 11/760,705, filed on Jun. 8, 2007, now U.S. Pat. No. 8,562,338, issued Oct. 22, 2013; U.S. application Ser. No. 11/760,701, filed on Jun. 8, 2007; and U.S. patent application Ser. No. 11/760,612, filed on Jun. 8, 2007, now U.S. Pat. No. 8,075,306, issued Dec. 13, 2011; the contents of each of which are incorporated herein by reference.

BACKGROUND OF THE INVENTION

The present invention relates generally to the field of orthodontics, and more particularly to a system and method for detecting positional differences between different models of a patient's teeth, as well as deviations from a planned course of treatment to gradually reposition teeth.

An objective of orthodontics is to move a patient's teeth to positions where function and/or aesthetics are optimized. Traditionally, appliances such as braces are applied to the patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, Calif., under the tradename Invisalign® System. The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools. The design of the aligners can rely on computer modeling of a series of planned successive tooth arrangements, and the individual aligners are designed to be worn over the teeth and elastically reposition the teeth to each of the planned tooth arrangements.

While patient treatment and tooth movements can be planned prospectively, in some cases orthodontic treatment can deviate from the planned treatment or stages. Deviations can arise for numerous reasons, and can include biological variations, poor patient compliance, and/or factors related to biomechanical design. In the case of aligners, continued treatment with previously designed and/or fabricated aligners can be difficult or impossible where a patient's teeth deviate substantially from the planned treatment course. For example, subsequent aligners may no longer fit the patient's teeth once treatment progression has deviated from the planned course.

Because detecting a deviation from planned treatment most typically relies on visual inspection of the patient's teeth or observation of appliances no longer fitting, treatment can sometimes progress significantly off track by the time a deviation is detected, thereby making any required corrective measures more difficult and/or substantial. Earlier and better off track determinations would, therefore, be beneficial in order to recalibrate the fit of the aligner device on the teeth. Accordingly, improved methods and techniques of detecting and correcting treatment that has deviated from planned or desired treatment course would be desirable, particularly methods allowing early detection of treatment deviation.

SUMMARY OF THE INVENTION

The present invention provides improved systems and methods detecting positional differences between different models of a patient's teeth. Such methods and systems can include automatic detection of deviations from an orthodontic treatment plan, tracking a patient's progress according to a planned treatment, and can further include incorporating enhanced tracking techniques into treatment delivery and management. If necessary, revising or modifying the patient's treatment plan based on a determination that treatment has progress off track can be accomplished. Information obtained according to the invention techniques can be used, for example, to more actively and/or effectively manage delivery of orthodontic treatment, increasing treatment efficacy and successful progression to the patient's teeth to the desired finished positions.

Thus, in one aspect, the present invention includes systems and methods for detecting deviations from an orthodontic treatment plan. A method can include, for example, receiving a tracking model comprising a digital representation of an actual arrangement of a patient's teeth after an orthodontic treatment plan has begun for the patient; performing a matching step between individual teeth in a plan model and the tracking model; comparing the tracking model with the plan model; and detecting one or more positional differences between the actual arrangement of the patient's teeth and the pre-determined planned arrangement of the patient's teeth.

The present invention further includes systems and methods for managing delivery and patient progression through an orthodontic treatment plan. Such a method can include, for example, providing an initial treatment plan for a patient; providing a plurality of orthodontic appliances; and tracking progression of the patient's teeth along the treatment path.

A method and system according to another embodiment of the present invention can include receiving a tracking model comprising a digital representation of an actual arrangement of a patient's teeth after an orthodontic treatment plan has begun for the patient for comparison to a plan model (e.g., including a pre-determined planned arrangement of the patient's teeth); performing an alignment step between the plan model and the tracking model using partial regions beyond a tooth crown of each of the plan model and the tracking model such that stationary elements of each of the plan model and the tracking model are aligned with one another; and detecting one or more positional differences between the actual arrangement of the patient's teeth and the pre-determined planned arrangement of the patient's teeth.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
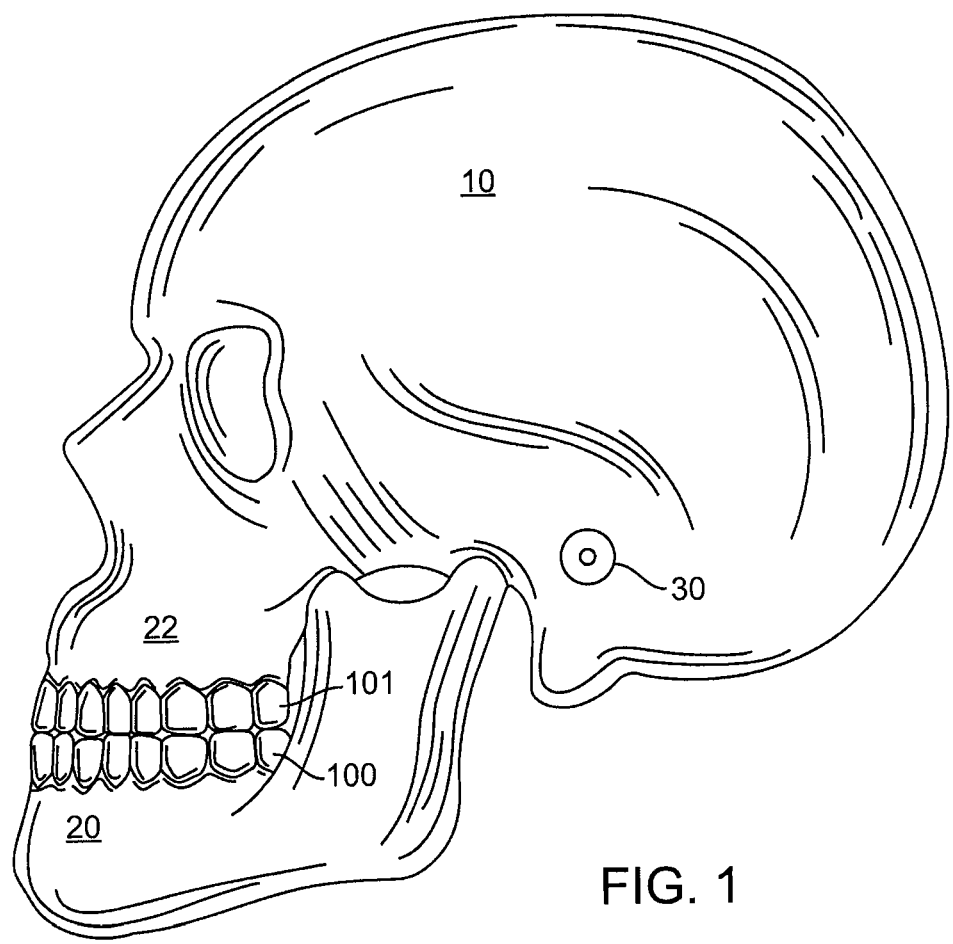
FIG. 1 is a diagram showing the anatomical relationship of the jaws of a patient.

The invention described herein provides improved and more automated systems and methods detecting positional differences between different models of a patient's teeth. The present invention can include tracking a patient's progress according to a planned treatment, incorporating enhanced tracking techniques into treatment delivery and management, and, if necessary, revising or modifying the patient's treatment plan based on a determination that treatment has progressed off track. Systems and methods of treatment progress tracking and revised planning can be included in a variety of orthodontic treatment regimens. For example, the progress tracking and revised planning features can be optionally included and incorporated into other aspects of treatment according to the Invisalign® System. Treatment can be pre-planned for administering to a patient in a series of one or more phases, with each phase including a set of appliances that are worn successively by the patient to reposition the teeth through planned arrangements and eventually toward a selected final arrangement. Progress tracking, according to the present invention, is incorporated into the pre-planned treatment for monitoring and management, and to provide enhanced detection and feedback as to whether treatment is progressing on track.

Model comparison and/or tracking steps according to the present invention can occur at any point during treatment but will typically be scheduled to correspond with a patient completing a pre-planned phase of treatment (e.g., wearing each appliance in a designated set). For example, once initial staging of a patient's teeth is completed (e.g., modeling of a patient's initial, intermediate, and final teeth arrangements) and a treatment plan has been devised, a dental practitioner can be sent a set of one or more appliances to be administered to the patient in the first phase of treatment. After the last appliance in the set is administered to the patient, an image of the patient's teeth in their positions following administration of the first set of appliances can be taken (e.g., using scan techniques, impression techniques, etc.). From the image of the patient's teeth in their current position, an assessment can be made as to how the treatment is tracking relative to original treatment projections. If there is a substantial deviation from the planned treatment path, then corrective action can be taken, for example, in order to achieve the original designed final position. Treatment then progresses to the next phase, where either the treatment can be finalized if the intended final positions are reached, or a subsequent set of appliances can be sent to the practitioner for administration to the patient. The subsequent set of appliances can be based on the initial treatment plan if treatment is progressing on track, or can be based on a revised or modified treatment plan when a determination is made that treatment is off track.

Methods and techniques for comparing tooth models for positional differences of the teeth and/or tracking tooth movement progress through a planned treatment are generally referred to herein as "teeth matching" or "bite matching." For example, comparison or matching techniques described herein can include matching teeth from the a model of the patient's teeth that may have been used for treatment planning or staging incremental movements of the patient's teeth according to a planned orthodontic treatment, to a new model of the teeth taken after treatment has begun. An off-track determination can be followed by "re-setting" to the actual position of the teeth as defined by data represented in the progress scan, the original data of the teeth (i.e., segmented models from initial treatment plan), thereby allowing preservation of the initially selected final target position of the teeth. In other words, the original data set, which contains with it an established target arrangement, can be reused by repositioning the teeth arrangement according to the positions of the (same) teeth captured in the progress scan. In so doing, a new planned path to go from the current teeth arrangement to the target teeth arrangement can be recreated without having to change the originally established target arrangement.

Comparison and matching according to the present invention can include using automatic alignment and matching techniques including several general steps. According to such teeth matching techniques, a tracking model or progress scan model is automatically aligned to a plan model, and teeth of the two models are matched. This step allows finding each tooth's position in the tracking model. Next, stationary and near-stationary teeth are detected, e.g., either by analysis of the planned teeth movements, or by statistical analysis. The result can include a set of stationary references for computing of teeth movements. Next, the measurement references (e.g., archform and occlusal plan) can be built from the plan model, and the planned and achieved tooth movement can be measured with respect to those references. Using such teeth matching techniques provides significant advantages in terms of more automation and efficiency as there is no need to re-segment and process the new scan of the teeth, and in terms of efficacy in overall treatment since the initial final arrangement is preserved, even if the patient progresses off track.

Incorporating the inventive techniques and tracking methods described herein in managing delivery/modification would provide various advantages, including earlier detection of treatment deviations, allowing earlier remedial measures to be taken, if necessary, to avoid undesirable treatment outcomes and preservation of initial treatment goals, thereby ultimately allowing for more effective treatment and better clinical outcomes. Furthermore, treatment efficiency and efficacy can be increased by better avoidance of inefficient and/or undesirable treatment "detours." Additionally, improved monitoring and tracking, as described, is more objective and reliable, and less qualitative in nature than the common practice of visually identifying off-track progress. This reduces the inter-clinician variability and reduces the dependency of accurate detection on clinician experience. As such, currently described inventive methods and techniques can inspire more confidence in both patients and practitioners, including practitioners that may be less experienced with a given treatment method and/or less confident in their abilities to clinically detect off-track progression, or even more experienced practitioners who desire more detailed monitoring, for example, in cases involving more difficult and/or less predictable movements.

FIG. 1 shows a skull 10 with an upperjaw bone 22 and a lowerjaw bone 20. The lowerjaw bone 20 hinges at a joint 30 to the skull 10. The joint 30 is called a temporal mandibular joint (TMJ). The upperjaw bone 22 is associated with an upper jaw 101, while the lower jaw bone 20 is associated with a lower jaw 100. A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
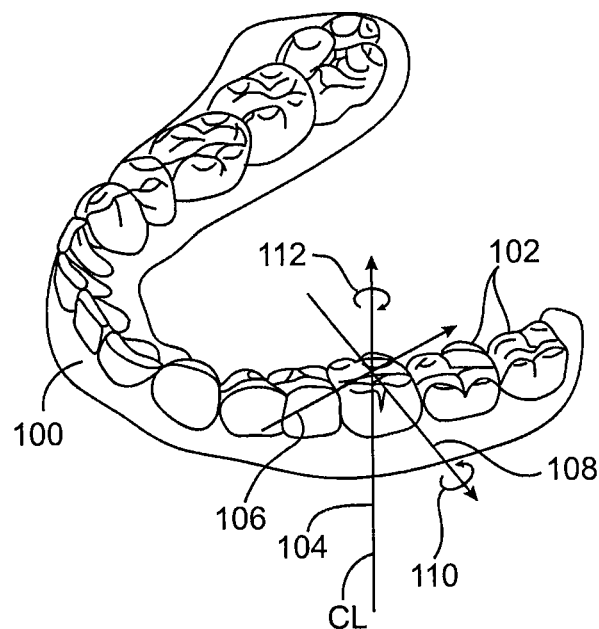
FIG. 2A illustrates in more detail the patient's lower jaw and provides a general indication of how teeth may be moved according to an embodiment of the present invention.

Referring now to FIG. 2A, the lower jaw 100 includes a plurality of teeth 102. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may-be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 112. Thus, all possible free-form motions of the tooth can be performed.

Figure 2B:
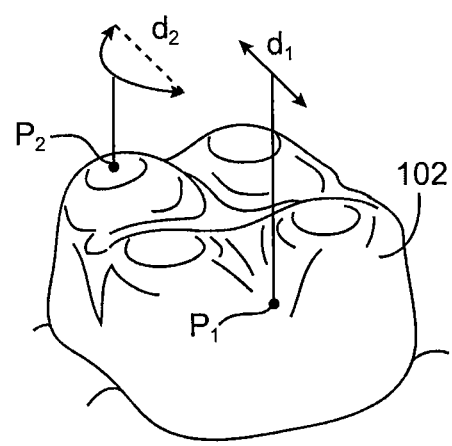
FIG. 2B illustrates a single tooth from FIG. 2A and defines determination of tooth movement distance according to an embodiment of the present invention.

FIG. 2B shows how the magnitude of any tooth movement may be defined in terms of a maximum linear translation of any point P on a tooth 102. Each point (e.g., P1 and P2) will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitrary point P2 may travel along a path including one or more than one curves or acute angles or the like, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

Figure 2C:
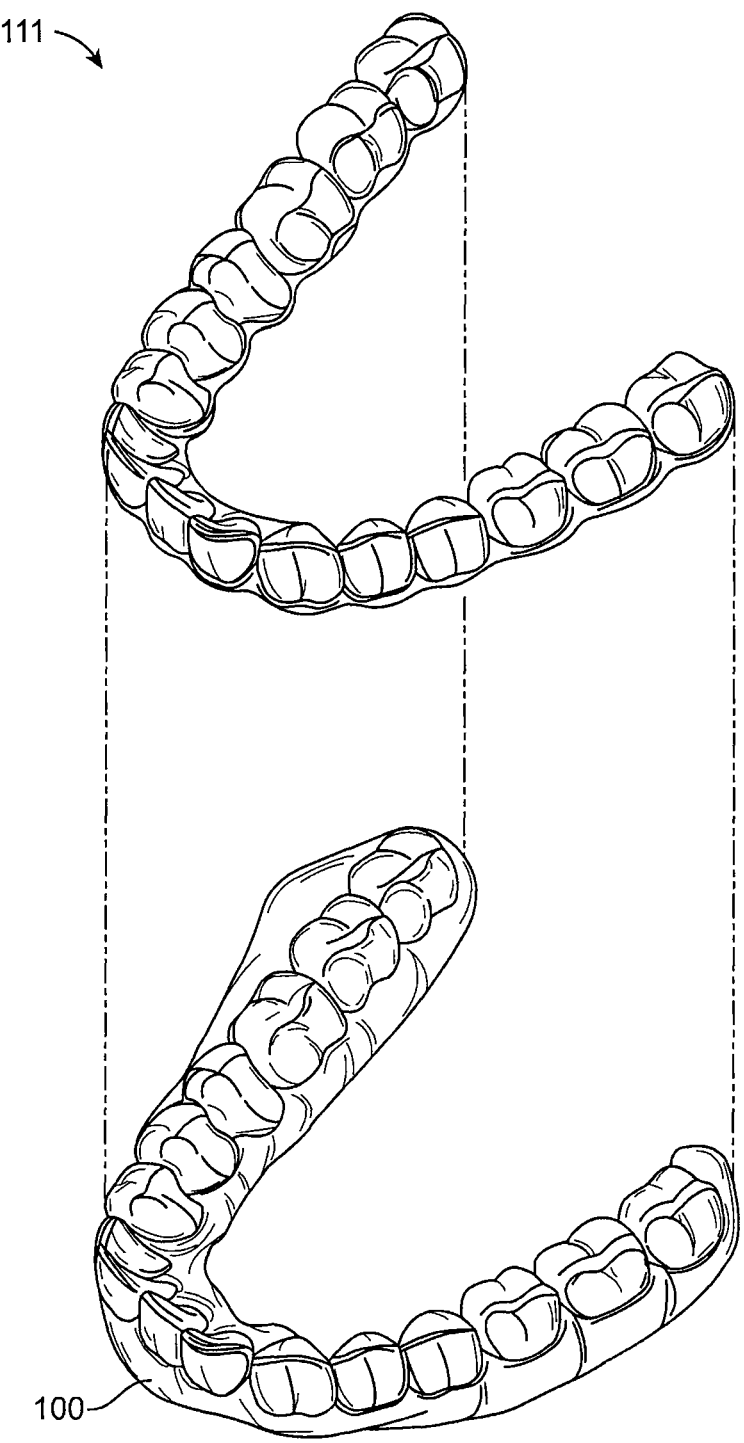
FIG. 2C illustrates the jaw of FIG. 2A together with an incremental positioning adjustment appliance according to an embodiment of the present invention.

FIG. 2C shows one adjustment appliance 111 which is worn by the patient in order to achieve an incremental repositioning of individual teeth in the jaw as described generally above. The appliance can include a shell (e.g., polymeric shell) having teeth-receiving cavities that receive and resiliently reposition the teeth. Such appliances, including those utilized in the Invisalign® System, as well as treatment planning aspects, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com").

As set forth in the prior applications, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt or has resulted in the maximum allowable tooth movement for that given stage. A plurality of different appliances (e.g., a set) can be designed and even fabricated prior to the patient wearing any appliance of the plurality. At that point, the patient replaces the current appliance with the next appliance in the series until no more appliances remain. The appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 3:
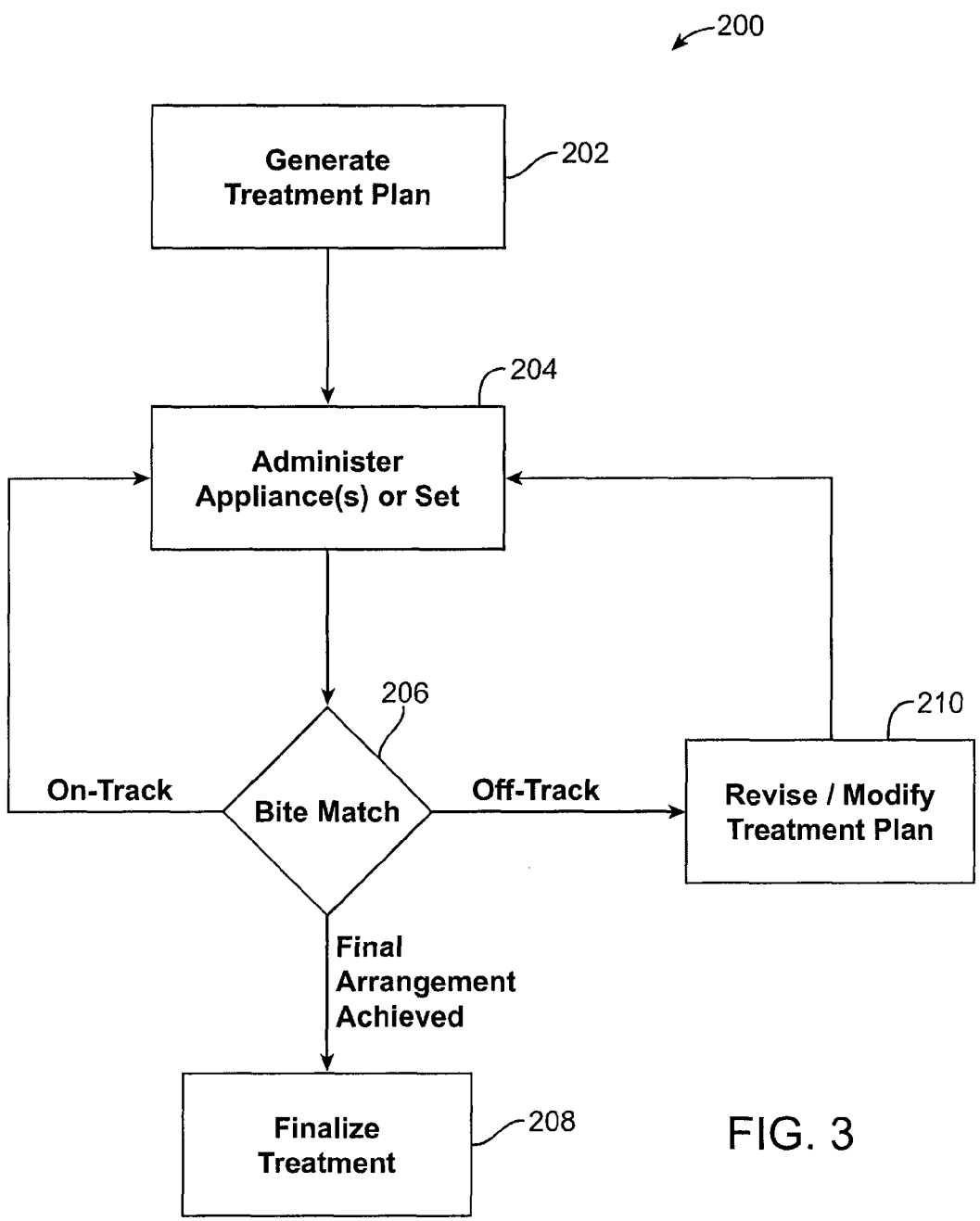
FIG. 3 shows generating and administering treatment according to an embodiment of the present invention.

Referring to FIG. 3, a method 200 according to the present invention is illustrated. Individual aspects of the process are discussed in further detail below. The process includes generating a treatment plan for repositioning a patient's teeth (Step 202). Briefly, a treatment plan will include obtaining data comprising an initial arrangement of the patient's teeth, which typically includes obtaining an impression or scan of the patient's teeth prior to the onset of treatment. The treatment plan will also include identifying a final or target arrangement of the patient's teeth that is desired, as well as a plurality of planned successive or intermediary tooth arrangements for moving the teeth along a treatment path from the initial arrangement toward the selected final or target arrangement. Appliances can be generated based on the planned arrangements and administered to the patient (Step 204). The appliances are typically administered in sets or batches of appliances, such as sets of 2, 3, 4, 5, 6, 7, 8, 9, or more appliances, but are not limited to any particular administrative scheme. After the treatment plan begins and following administration of appliances to the patient, teeth matching is done to assess a current and actual arrangement of the patient's teeth compared to a planned arrangement (Step 206). If the patient's teeth are determined to be "on-track" and progressing according to the treatment plan (e.g., the patient's teeth are moving at a rate and/or in accordance with the treatment plan), then treatment progresses as planned. If the patient's teeth have reached the initially planned final arrangement, then treatment progresses to the final stages of treatment (Step 208). Where the patient's teeth are determined to be tracking according to the treatment plan, but have not yet reached the final arrangement, the next set of appliances can be administered to the patient (repeat Step 204, according to the initial treatment plan). If, on the other hand, the patient's teeth are determined at the teeth matching step (Step 206) not to be tracking with the treatment plan (e.g., the patient's teeth are not moving at a rate and/or in accordance with the treatment plan), then treatment is characterized as "off-track" and an assessment is made as to how further treatment of the patient will proceed. Typically, a revised treatment plan will be generated (Step 210), and may be selected, for example, to reposition the teeth from the current position to a final position, which may be the same destination as the initially determined final position according to the initial treatment plan.

Systems of the present invention can include network based systems, including a data network and a server terminal operatively coupled to the network. One or more client terminals can be included and operatively coupled to the network. Systems can optionally include more stand-alone or non-network based systems, including computers and software packages designed to at least partially operate independent of a data network and in which various steps of the currently described methods can be accomplished in an automated fashion at a remote location (e.g., practitioner's office).

Figure 4:
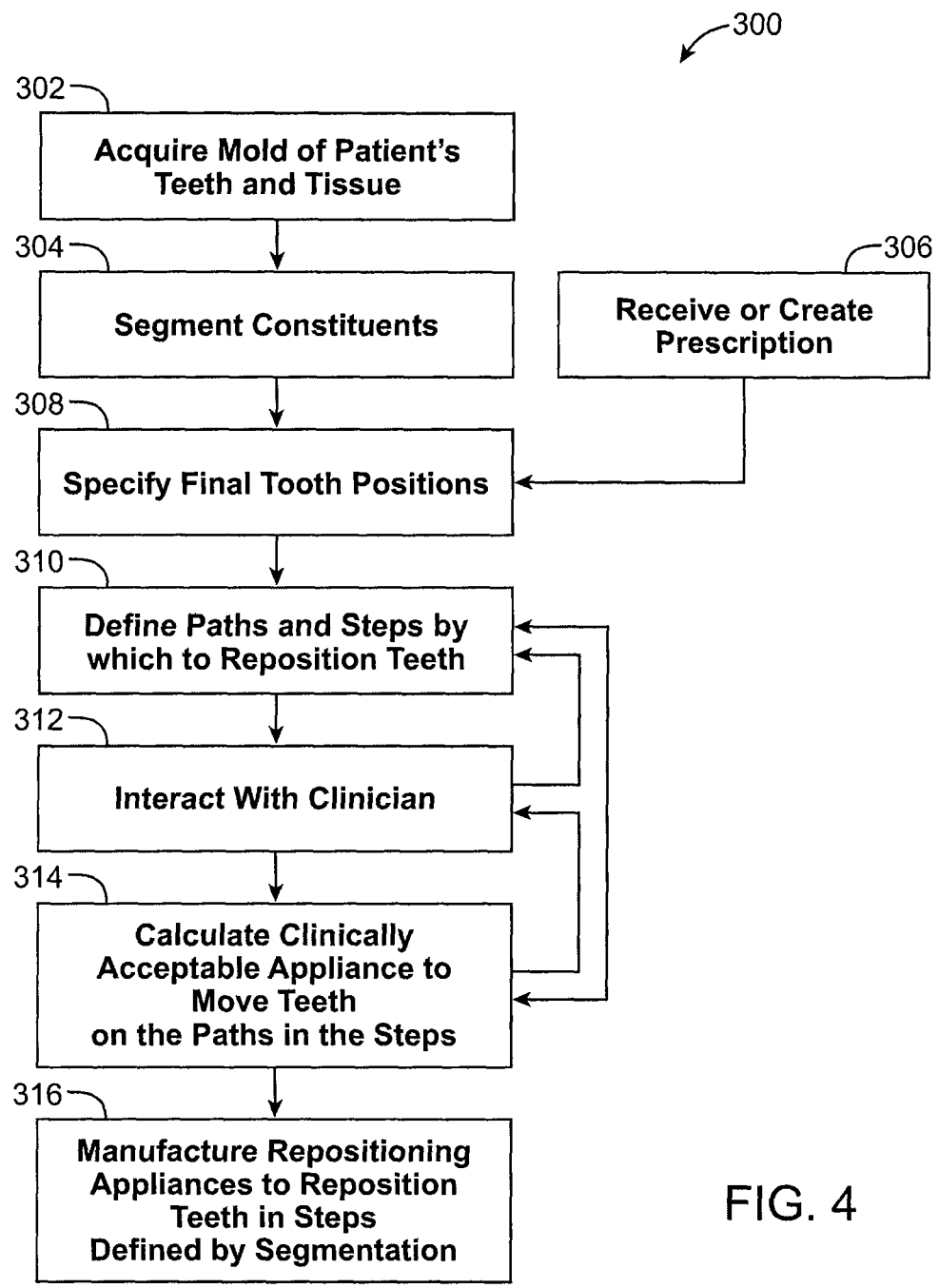
FIG. 4 illustrates generating a treatment plan according to an embodiment of the present invention.

FIG. 4 illustrates the general flow of an exemplary process 300 for defining and generating a treatment plan, including repositioning appliances for orthodontic treatment of a patient. The process 300 includes the methods, and is suitable for the apparatus, of the present invention, as will be described. The steps of the process can be implemented as computer program modules for execution on one or more computer systems.

As an initial step, a mold or a scan of patient's teeth or mouth tissue is acquired (Step 302). This generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents an initial (e.g., pretreatment) arrangement of the patient's teeth and other tissues.

The initial digital data set, which may include both raw data from scanning operations and data representing surface models derived from the raw data, is processed to segment the tissue constituents from each other (Step 304), including defining discrete dental objects. For example, data structures that digitally represent individual tooth crowns can be produced. In some embodiments, digital models of entire teeth are produced, including measured or extrapolated hidden surfaces and root structures.

Desired final position of the teeth, or tooth positions that are a desired and/or intended end result of orthodontic treatment, can be received, e.g., from a clinician in the form of a descriptive prescription, can be calculated using basic orthodontic prescriptions, or can be extrapolated computationally from a clinical prescription (Step 306). With a specification of the desired final positions of the teeth and a digital representation of the teeth themselves, the final position and surface geometry of each tooth can be specified (Step 308) to form a complete model of the teeth at the desired end of treatment. The result of this step is a set of digital data structures that represents a desired and/or orthodontically correct repositioning of the modeled teeth relative to presumed-stable tissue. The teeth and surrounding tissue are both represented as digital data.

Having both a beginning position and a final target position for each tooth, the process next defines a treatment path or tooth path for the motion of each tooth (Step 310). This includes defining a plurality of planned successive tooth arrangements for moving teeth along a treatment path from an initial arrangement to a selected final arrangement. In one embodiment, the tooth paths are optimized in the aggregate so that the teeth are moved in the most efficient and clinically acceptable fashion to bring the teeth from their initial positions to their desired final positions.

At various stages of the process, the process can include interaction with a clinician responsible for the treatment of the patient (Step 312). Clinician interaction can be implemented using a client process programmed to receive tooth positions and models, as well as path information from a server computer or process in which other steps of process 300 are implemented. The client process is advantageously programmed to allow the clinician to display an animation of the positions and paths and to allow the clinician to reset the final positions of one or more of the teeth and to specify constraints to be applied to the segmented paths.

The tooth paths and associated tooth position data are used to calculate clinically acceptable appliance configurations (or successive changes in appliance configuration) that will move the teeth on the defined treatment path in the steps specified (Step 314). Each appliance configuration corresponds to a planned successive arrangement of the teeth, and represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with other steps, this calculation step can include interactions with the clinician (Step 312).

Having calculated appliance definitions, the process 300 can proceed to the manufacturing step (Step 316) in which appliances defined by the process are manufactured, or electronic or printed information is produced that can be used by a manual or automated process to define appliance configurations or changes to appliance configurations. Appliances according to the treatment plan can be produced in entirety, such that each of the appliances are manufactured (e.g., prior to treatment), or can be manufactured in sets or batches. For example, in some cases it might be appropriate to manufacture an initial set of appliances at the outset of treatment with the intention of manufacturing additional sets of appliances (e.g., second, third, fourth, etc.) after treatment has begun (e.g., as discussed further herein). For example, a first set of appliances can be manufactured and administered to a patient. Following administration, it may be desirable to track the progression of the patient's teeth along the treatment path before manufacturing and/or administering subsequent set(s) of appliances.

Generating and/or analyzing treatment plans, as discussed herein, can include, for example, use of 3-dimensional orthodontic treatment planning tools such as Treat® from Align Technology, Inc. or other software available from eModels and OrthoCAD, among others. These technologies allow the clinician to use the actual patient's dentition as a starting point for customizing the treatment plan. The Treat® technology uses a patient-specific digital model to plot a treatment plan, and then use a scan of the achieved or actual treatment outcome to assess the degree of success of the outcome as compared to the original digital treatment plan as discussed in U.S. patent application Ser. No. 10/640,439, filed Aug. 21, 2003 and U.S. patent application Ser. No. 10/225,889 filed Aug. 22, 2002. (see also, below).

In some cases, patients do not progress through treatment as expected and/or planned. For example, in some instances a patient's progression along a treatment path can become "off-track" or will deviate from an initial treatment plan, whereby an actual tooth arrangement achieved by the patient will differ from the expected or planned tooth arrangement, such as a planned tooth arrangement corresponding to the shape of a particular appliance. A determination that the progression of a patient's teeth is deviating or not tracking with the original treatment plan can be accomplished in a variety of ways. As set forth above, off-track deviations can be detected by visual and/or clinical inspection of the patient's teeth. For example, a substantial off track deviation from the expected or planned treatment may become apparent when the patient tries to wear a next appliance in a series. If the actual tooth arrangement substantially differs from the planned arrangement of the teeth, the next appliance will typically not be able to seat properly over the patient's teeth. Thus, an off-track deviation may become substantially visually apparent to a treating professional, or even to the patient, upon visual or clinical inspection of the teeth.

Detecting deviations from a planned treatment, however, can be difficult, particularly for patients as well as certain dental practitioners, such as those with more limited experience in orthodontics, certain general dentists, technicians, and the like. Additionally, deviations that have progressed to the point that they are visually detectable clinically are often substantially off track with respect to the planned treatment, and earlier means of off-track detection is often desired. Thus, detecting deviations from a treatment plan can also be accomplished by comparing digital models of the patients teeth, and can often detect deviations from a treatment plan before the deviation becomes substantially apparent by visual or clinical inspection, advantageously resulting in reduced costs, treatment plan times and patient discomfort.

One exemplary known computer based teeth matching process includes comparing an actual position of the teeth relative to a planned or expected position using comparison of two processed or segmented scans of the patient's teeth—a processed plan treatment and a processed (e.g., segmented) tracking model. See, e.g., commonly owned U.S. Pat. Nos. 7,156,661 and 7,077,647 for discussion of comparing actual positions of the teeth relative to a planned or expected position using a processed (e.g., segmented) scan of the teeth positions following initiation of treatment.

Another exemplary computer based teeth matching process includes comparing a previously segmented planned model of the patient's teeth to an unsegmented or non-segmented representation of an actual arrangement of the patient's teeth, or tracking model, that has been further processed including marking of Facial Axis of the Clinical Crown (FACC) for each teeth in the tracking model. See, e.g., commonly owed U.S. application Ser. No. 11/760,612, entitled "System and Method for Detecting Deviations During the Course of an Orthodontic Treatment to Gradually Reposition Teeth," filed Jun. 8, 2007, for further discussion of comparing a non-segmented, FACC marked, representation of an actual arrangement of a patient's teeth after treatment has begun to a previously segmented model of the patient's teeth.

The present invention includes automatic alignment and matching systems and methods of measuring and evaluating tooth movements based on matching a patient's impression model or tracking model obtained during treatment or after tooth movement treatment has begun, with a plan model from treatment planning. By automatic alignment and matching of the tracking model and the plan model, a planned tooth movement and actually achieved tooth movement during a stage of treatment can be compared and evaluated.

Automatic alignment and matching according to the present invention includes several general steps. First, a tracking model is automatically aligned to a plan model, and teeth of the two models are matched. This step allows finding each tooth's position in the tracking model. Second, stationary and near-stationary teeth are detected, e.g., either by analysis of the planned teeth movements, or by statistical analysis. The result can include a set of stationary references for computing of teeth movements. Third, the measurement references (e.g., archform and occlusal plane) can be built from the plan model, and the planned and achieved tooth movement can be measured with respect to those references. Such planned and achieved tooth movement measurements constitute valuable information which, as mentioned, can be used for treatment progress tracking, monitoring, and calibration, as well as orthodontic/biology study and research, tooth movement velocity study, appliance performance analysis, and the like.

Figure 5:
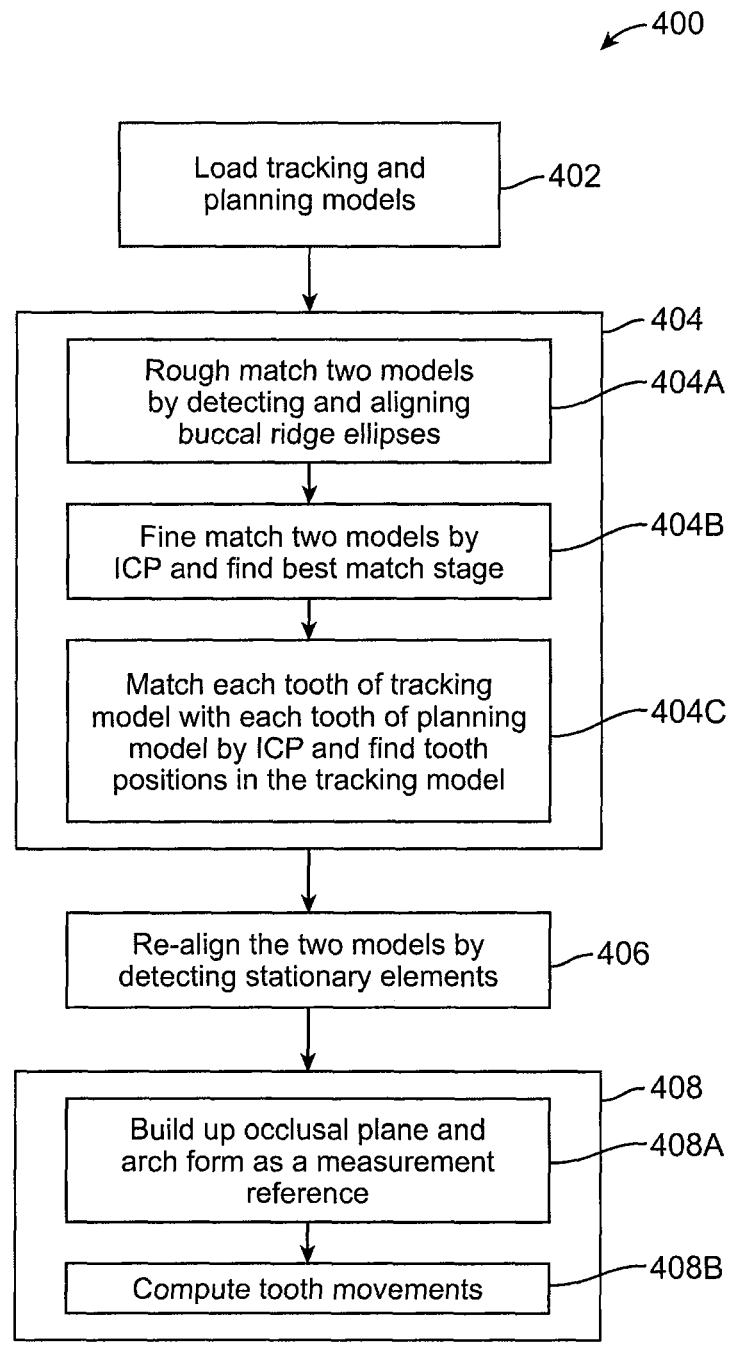
FIG. 5 illustrates a process including teeth matching according to one embodiment of the present invention.

An exemplary method of automatic alignment and matching of a tracking model and treatment plan model according to the present invention is described with reference to FIG. 5. As shown, FIG. 5 illustrates the general flow of an exemplary process 400 for detecting deviations from a planned treatment. Steps of the process 400 can be implemented by a computer based system, such as computer program modules for execution on one or more computer systems.

As an initial step, a tracking model and one or more planning models of the patient's teeth are obtained as described further herein and can then be received by or loaded into a system for automatic alignment and matching according to techniques of the present invention (Step 402). The tracking model is a three-dimensional digital model, i.e. a digital representation, of a patient's teeth during treatment. The tracking model may be acquired by various methods, including scanning the patient's teeth or impressions of the patient's teeth, or via any other direct or indirect method of acquiring a three-dimensional digital model of a patient's teeth, such as 3D laser scanning, 3D CT scanning, stereophotogrammetry, intra-oral direct dental scanning, and destructive scanning techniques. The one or more plan models are three-dimensional digital models of desired and/or actual teeth arrangements in accordance with the treatment plan as described above (see, e.g., FIG. 4). For example, the one or more plan models (e.g., segmented models) may include a digital model of the patient's initial teeth arrangement, a planned intermediate arrangement of the patient's teeth, and/or a planned target or final arrangement of the patient's teeth. Automatic alignment and matching, according to methods of the present invention, typically includes comparison of an unsegmented tracking model with a plan model that have already been processed and segmented during treatment planning stages.

After loading the tracking and one or more plan models, a matching step is performed between a plan model and the tracking model (Step 404). Matching according to Step 404 can include first performing a rough matching step where the teeth of models are roughly aligned. For example, the teeth of the tracking model can be roughly matched to (i.e., aligned with) the teeth of the plan model. In one embodiment, rough matching can be accomplished by detecting the buccal ridge ellipse of each of the tracking model and the plan model and aligning the detected buccal ridge ellipses with one another (Step 404A). Following rough matching, the two models can be fine aligned (i.e., further aligned to achieve a closer match between the two models) by the application of surface matching algorithms, feature matching algorithms, and the like (Step 404B). 3D model registration algorithms may also be employed. In an embodiment of the present invention, the "Iterative Closest Point" (ICP) surface matching algorithm is used. Fine alignment can include matching the tracking model to a plurality of plan models, e.g., each representing different or progressive stages of a planned treatment, so as to find the best match between a particular one of the one or more plan models and the tracking model (Step 404B). Fine alignment can further include matching individual teeth of the plan model with the tracking model (e.g., the plan model found via Step 404B that best matches the tracking model) (Step 404C). Such individual teeth matching can also be implemented by applying the "Iterative Closes Point" (ICP) algorithm tooth by tooth. As a result of the matching step 404, including rough matching, fine alignment and individual teeth matching, each tooth in the plan model can be aligned to corresponding position in the tracking model. So the positions of the teeth in the tracking model can be found, with the advantage of using only of non-segmented tracking model and fully automatic operation without human interaction.

Next, the process may include an additional matching (i.e., re-alignment) step, including comparing the tracking model with the plan model, so as to detect stationary elements (e.g., stationary teeth) of the patient's dentition such that positions of non-stationary teeth can be measured relative to the detected stationary elements (Step 406). Such a comparison can include comparing or superimposing the tracking model with a plan model (any plan model, including the best match planning model, may be used). The stationary elements can be teeth determined as having minimal movement according to the treatment plan or as detected by statistical analysis. Because the teeth positions in the tracking model are known from the matching step described above (Step 404), the alignment of the tracking model to the plan model can be accomplished, in one embodiment, by optimizing the square distance of all vertices in two models (one in the tracking model, another in the plan model), where the vertices are weighted according to their probability of being associated with stationary teeth.

Next, the process can compare planned tooth positions with actually achieved tooth positions (Step 408) so as to detect one or more positional differences between the actual and planned movement of the patient's teeth. Such a comparison can include building up an occlusal plane and archform as a measurement reference (Step 408A) and computing tooth movements relative to this measurement reference (Step 408B).

Iterative Closest Point Algorithm

As described above, fine matching of two models (Step 404B) and matching each tooth of a plan model with tracking model (Step 404C) can include utilization of a 3D model registration algorithm. One such algorithm that can find use in the methods of the present invention is an "Iterative Closest Point" (ICP) algorithm.

In general, surface matching (e.g., model registration, model matching, point registration etc.) is a common and challenging problem in many computer graphics applications. ICP is an algorithm well suited for surface matching. The basic idea for utilizing ICP according to the present invention is to find closest point pairs between two models, or between corresponding teeth in each of two models, assuming that after matching every pair should become one point. The points can be, for example, vertexes located on a surface of a model. The surfaces may be surfaces of the teeth of the model, surfaces of fixed accessories to teeth, surfaces of the gingiva of the model, and the like. Then, the transformation is computed to minimize the distances between the pairs of points. The general steps of the ICP algorithm are as follows: selecting source points (from at least one or of a model); determining matching points on another model by finding points on at least one surface of the other model (e.g., mesh) that are closest to points on the at least one surface of the model; rejecting certain point pairs, such as point pairs constituting outlier points; assigning an error metric to distances between points in pairs; minimizing the error metric by computing a rigid body transform and applying it to one of the models and make that model moved to new position. Then, the above steps are repeated for the moved model: searching new point pairs; assigning new error metric and computing new transformation by minimizing error metric. Repeat these steps until the error has converged or maximum iteration number achieved.

According to one embodiment of the present invention, the following detailed algorithms can be used. First, a coarse-fine volume (CFV) data structure can be used to find closest points. The CFV data structure can be a two level, 3 dimensional array that stores the closest vertex of each point in the neighborhood of the model. Advantageously, CFV data structures are very fast and memory efficient. Second, an adaptive matching range can be used to reject outlier point pairs. The matching range is gradually reduced and adapted to the level of noise. Accordingly, the search for closest points encompasses both "coarse to fine point matching" and "reject outlier" features. Third, the distance from a point to a fixed plane can be used as the error metric. Fourth, singular value decomposition (SVD) can be used for the rigid body transform computation.

CFV Data Structure

The CFV data structure and its use according to the present invention are further described. Conventionally, a 3D model is represented as sets of vertices and triangular faces. A model may contain numerous (e.g., thousands, millions, etc.) vertices and triangles. It may take only several milliseconds to find one pair of points from two models, but it will take seconds, even minutes to find thousands of pairs. It's even more time consuming to apply the ICP algorithm because the ICP algorithm requires dozens to hundreds of iterations, where each iteration requires thousands of searches for point pairs.

Different algorithms have developed to speed up this process, like octree, k-d tree. The basic idea of these different algorithms is to organize the scatted vertices in space in such a way that for each search only a small number of comparisons is needed. In one embodiment of the present invention, 3 dimensions space is divided into small cubes and represented by a 3 dimensions array in software program. Each element of the array stores the closest vertex from the center of cube to the model. That means, given a point in 3D, the closest vertex to a model can be immediately found, which is the only vertex in the cube the point is located. However, when only a limited amount of memory is available to store points in 3D, a "coarse to fine" approach can be used. The use of a "coarse to fine" approach advantageously reduces the memory requirements for storing points in 3D.

Figure 6:
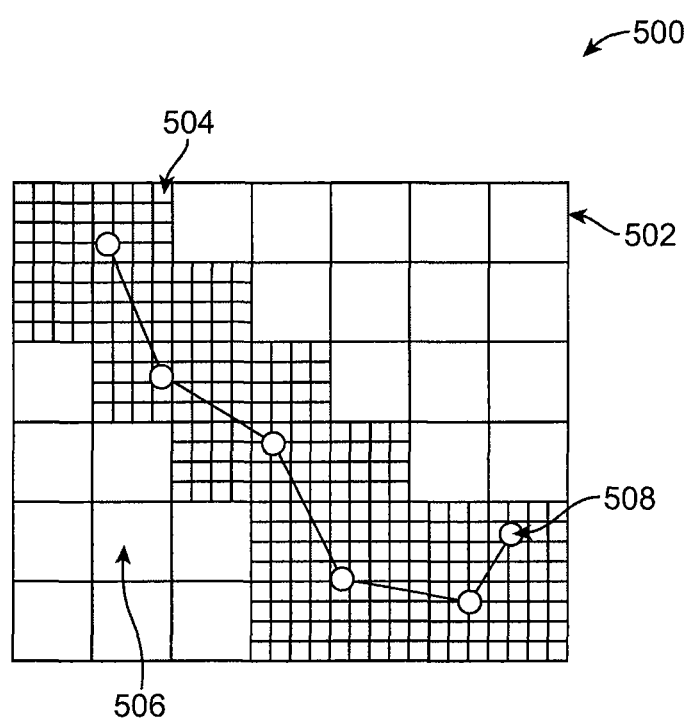
FIG. 6 illustrates a data structure according to an embodiment of the present invention.

FIG. 6 is a 2D illustration of a CSV 3D data structure 500 in accordance with an embodiment of the present invention. The data structure 500 includes a bounding cube 502 that encompasses all vertices 502 in the model. The bounding cube can be uniformly divided into many coarse cubes 506. Each coarse cube 506 that is near a vertex 502 of model can be divided into many fine cubes 504. The data structure 500 can advantageously be a CFV data structure. For each coarse and/or fine cube, the vertex that is closest to the centre of the cube is stored. Also, the parent coarse cube also stores the reference to its fine cubes which are represented by a 3 dimensions array.

For a given point in 3D, its closest vertex to the model then is the closest vertex stored in the coarse or fine cube it located. For points other than cube centers, there may be error in distance to the closest vertex of the mesh since every cube stores only the closet vertex to its centre. However, the coarse cube is far from the model, so the error is small compared to the distance to the vertex. For fine cube, its size is small enough, so the error is also small compared to the distance. In our application, i.e. the ICP algorithm, the distance computed is accurate enough, both for coarse or fine cube.

In accordance with one embodiment of the present invention, the data structure 500 is built by performing the following steps:
1. Initialize coarse cubes and set a reference to the closest vertex for these cubes as "NULL".
2. For each vertex in the model, find the coarse cube it is located and the neighboring cube(s).
3. If the located-cube and neighboring coarse cube(s) has no set reference to a closest vertex, then set the reference to the current vertex. Else, check whether the new vertex is closer to the cube's center. If true, replace the vertex reference by the new vertex reference.
4. For the coarse cube that the vertex located, subdivide it into fine cubes (which are also represented as 3 dimensions array), if not done before.
5. For each fine cube, check the distance of the cube center to the vertex, replace closest vertex reference if the new vertex is closer.

After the CFV data structure is constructed, it can be used to find the closest vertex from any given point 3D to the model. Advantageously, using the aforementioned data structure, a maximum of only 2 steps are needed to find the closest point for a given point in 3D; one step to acquire the reference set for a coarse cube. If there are fine cubes linked in the coarse volume, a second step is used to acquire the vertex reference by look-up the fine cube where the point is in.

Rejecting Outlier Point Pairs

In general, two 3D models typically are not identical since the scanning of the models can be performed from different positions or at different times; or models may be modified in the later processing procedures. In accordance with the present invention, teeth are usually moved during treatment, so models acquired at the beginning of the treatment and models acquired during the course of treatment are not likely to be the same. Also, tracking models generally represent raw data and thus usually contain data acquirement and scanning errors, extra material and noise. Accordingly, there is often some part in a model that cannot be matched to another model.

In an embodiment of the present invention, the parts of a model that cannot be matched to another model can be filtered out. A method for filtering out such parts is to employ an adaptive matching range. For example, for a given pair of points, if the distance between the pair of points is bigger than a predetermined distance (i.e., a matching range), the pair of points is considered to be an outlier point pair and therefore is not used for calculating the matching transformation. The matching range can be adaptive to the noise level in each iteration of ICP computation.

An exemplary adaptive matching range according to an embodiment of the present invention is defined by the formula:

$$MR_i = w \cdot MR_{i-1} + (1-w) \cdot (k \cdot D_{i-1} + R) \tag{1}$$

Where: $MR_i$ is a new matching range, $MR_{i-1}$ is a the matching range of a previous iteration, is the iteration, w ($0<w<1.0$) is a shrink coefficient, k is an error magnification coefficient, $D_{i-1}$ is a current average matching error, and R is a minimum match range, which has the same magnitude as the scanning error.

The initial value of the matching range, i.e., $MR_o$, is set large enough so that a large number of vertex pair, like 50% of all vertex in the model can be selected for the first iteration. Then, the matching range is gradually reduced due to the weight w<1.0. When the number of iterations approaches infinity, the matching range approaches:

$$k \cdot D_{i-1} + R \quad (2)$$

Here, D is the residual average matching error. So, even if D=0, the match range is still not zero, so some point pairs can always be selected. If D is large, then MR is also large. That means, for noisy data, the search range can be relatively large; on the other hand, for clean data, the search range can be relatively small.

Figure 7:
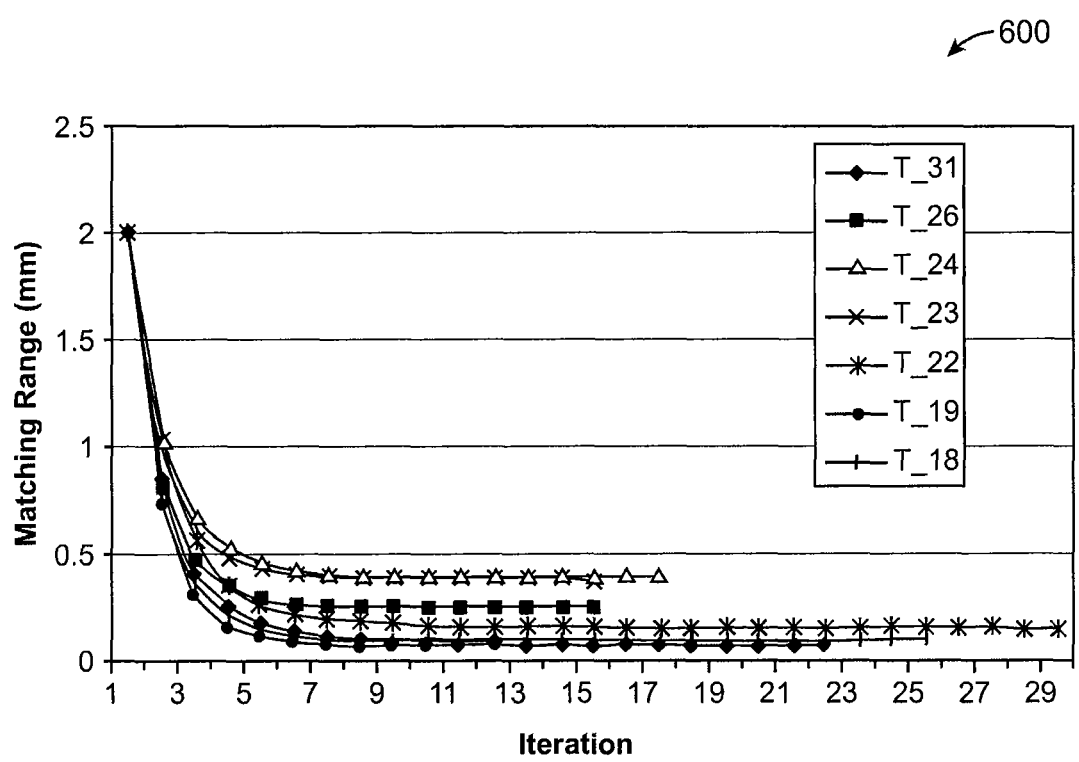
FIG. 7 illustrates a matching range for different teeth according to an embodiment of the present invention.

FIG. 7 illustrates, in accordance with an embodiment of the present invention, a graph 600 showing the changes in the matching range for different teeth, i.e., teeth numbered 18, 19, 22, 23, 24, 26 and 31. The x-axis of FIG. 7 represents the number of iterations of formula (1). The y-axis of FIG. 7 represents the resulting matching range in mm. The matching ranges for all teeth start at 2 mm and reached different final values, reflecting different levels of noise for each tooth.

Advantageously, by using an adaptive matching range, outlier point pairs can be effectively removed. When an adaptive matching range is used for matching a tracking model with a planning model, scanning errors, noise, and extra material due to attachments and the like can be automatically removed.

Error Metric of a Point Pair

In an embodiment of the present invention, an error metric is assigned to distances between point pairs and minimized for calculating the matching transformation. Conventionally, an error metric is calculated as the square distance of two points according to the following formula:

$$\text{Err} = \|P - Q\|^2 = (P - Q)^T (P - Q) \quad (3)$$

Where Err is the error metric, P is a first point in a point pair, and Q is a second point in the point pair.

Figure 8:
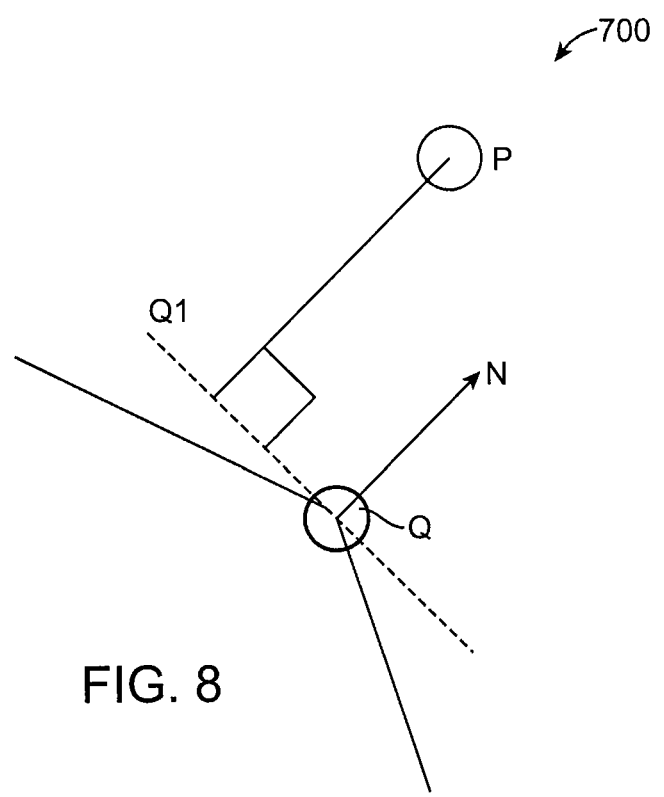
FIG. 8 illustrates a spatial reference diagram for "point to plane" calculations according to an embodiment of the present invention.

In an embodiment of the present invention, the error metric can be calculated using a "point to plane" distance. FIG. 8 illustrates a spatial reference diagram 700 showing a relationship between P, Q and a point $Q_1$. For each vertex (i.e., point) Q in a model; there is a normal vector N assigned to it that is normal to a surface of the model at which the vertex Q is located. Alternatively, the normal vector N can be equal to an average of at least some, or even all, vectors that are normal to model surfaces that neighbor the vertex Q. A plane is thus provided that intersects vertex Q and is perpendicular to the normal vector N. The error metric, in accordance with the "point to plane" distance, can then be calculated as:

$$\text{Err} = \|P - Q_1\|^2 = (P - Q_1)^T (P - Q_1) \quad (4)$$

Where P is a first point (i.e., vertex) in a point pair, Q is a second point (i.e., vertex) in the point pair, and $Q_1$ is the projected point of P into the plane provided that intersects Q and is perpendicular to the normal vector N.

Computing a Rigid Body Transform by SVD.

In an embodiment of the present invention, a rigid body transform is computed and applied to a model. Advantageously, "Singular Vale Decomposition" (SVD) can be used as the rigid body transform. The following algorithm can be used to compute, via SVD, the rigid-body transform:

Assume that all point pairs between two models are found as $$(P_i, Q_i), i=1, 2, \ldots N \quad (5)$$

Where $P_i$, is a point from a first of the two models for point pair i, $Q_i$, is a point from a second of the two models for point pair i, and N is the total number of point pairs. The rigid transformation between the resulting two sets of point can be estimated by minimizing the following cost function:

$$J = \sum_{i=1}^{N} \|P_i - Q_i\|^2 = \sum_{i=1}^{N} (P_i - Q_i)^T (P_i - Q_i) \quad (6)$$

The rigid transform between two models is:

$$Q_i = R \cdot P_i + T + \epsilon_i \quad (7)$$

Where R is a rotation matrix, T is a translation vector, $\epsilon_i$ is the error.

Define $$H = \sum_{i=1}^{N} P_i Q_i^T \quad (8)$$

If the singular value decomposition of H is $H = UAV^T$, then the rotation matrix R is $R = VU^T$, and the translation vector T is:

$$T = \overline{Q} - R * \overline{P} = \frac{1}{N} \sum_{i=1}^{N} Q_i - R * \frac{1}{N} \sum_{i=1}^{N} P_i \quad (9)$$

Details of using SVD for computing rigid body transformations as well as additional algorithms for computing rigid body transformations can be found in D. W Eggertl, A. Lorusso, R. B. Fisher: "Estimating 3-D rigid body transformations: a comparison of four major algorithms," Machine Vision and Applications, pp. 272-290, 1997, which is incorporated by reference herein in its entirety.

Matching of Tracking and Planning Models

In accordance with an embodiment of the present invention, a matching step 404 is performed between a planning model and the tracking model. The matching step 404 can include rough matching 404A, fine matching models and finding a best match stage 404B, and fine matching individual teeth of models and finding tooth positions 404C. One of the purposes of the matching step 404 is to determine the positions of the teeth in the impression model so that tooth movements can subsequently be determined based on these positions.

In an embodiment of the present invention, the previously discussed ICP algorithm is used to fine match a planning model and a tracking model. The ICP algorithm can be used to match the whole planning model and the tracking model, or be used to match individual teeth of the planning model with the tracking model, where teeth are not segmented out. In any event, before applying the ICP algorithm, a good initial match between the planning model and the tracking model can advantageously be determined; i.e., the planning model and the tracking model can be roughly aligned before the ICP algorithm is applied. This step is called "rough alignment" or "rough matching". Advantageously, applying a rough matching step before using the ICP algorithm increases the likelihood that minimization aspects of the ICP algorithm actually converge, converge on global minimal, and/or converge without requiring an undue number of iterations. More important, fully automatic rough matching algorithm can make all process automated, that can greatly reduce human operation time and errors.

After the tracking model and a planning model are roughly matched, the ICP algorithm can be used to finely match the tracking model and the planning model. In the case that there is more than one planning model, a plurality of planning models can undergo the rough matching and fine matching. The planning model that best matches the tracking model can be determined. Once the planning model that best matches the tracking model is determined, then the ICP algorithm can be used once more to finely match the teeth of that planning model and the tracking model. The position of the teeth in the tracking model can then computed, and the quality of the tooth matching can be evaluated.

Rough Matching

Conventional methods for performing rough matching include manually moving two models to roughly matching positions, or marking the same feature points in two models with subsequent alignment of these feature points. Example of feature points includes the corner point, intersection of two edges, dimple points or so on. Another example of feature points the FA point, which is the center pointer of "Facial Axis of Clinical Crown" (FACC) curve. Both of these conventional methods are heavily dependent on human operation and are not suitable for fully automatic data analysis.

Conventional methods for performing rough matching also include methods that are not dependent on human operation; i.e., fully automatic matching. These types of methods may be incorporated and are well suited for the present invention. Fully automatic 3D model matching approaches include:
1. Feature detection and matching (such as high-curvature points (i.e., corners), flat plane patches, edges, space curves and the like).
2. Translation invariant 2D image matching, like spin-image and Extended Gaussian Image (EGI).

Figure 9:
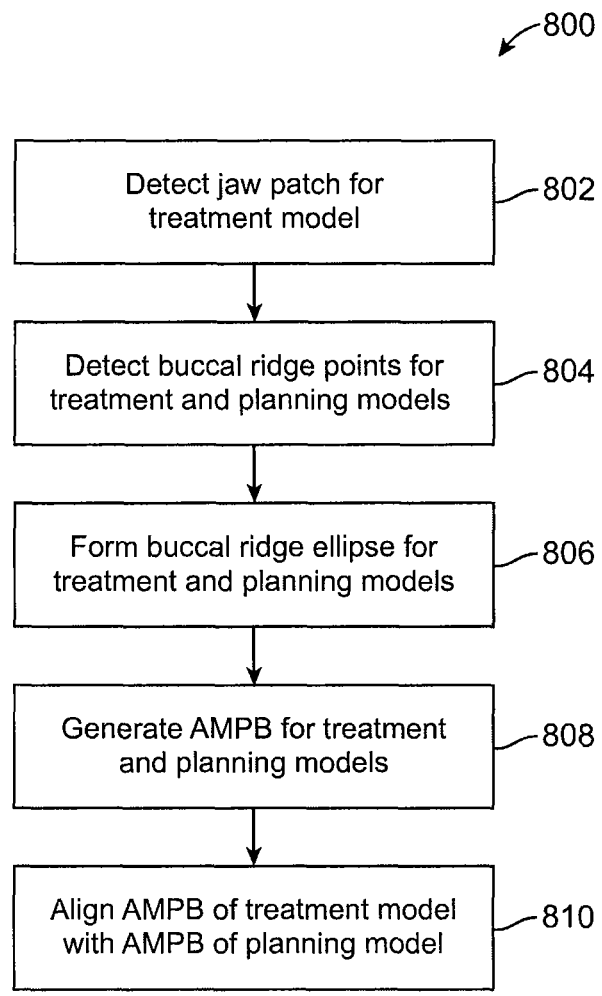
FIG. 9 illustrates a process for rough matching according to an embodiment of the present invention.

FIG. 9 illustrates a method for rough matching 800 in accordance with an embodiment of the present invention. The method for rough matching 800 utilizes feature detection, where the detected feature is a buccal ridge ellipse.

In a tracking or planning model, the teeth may or may not be segmented from the jaw. Commonly, teeth will not be segmented from jaw for tracking model. In the case that the teeth are not segmented from the jaw, the jaw patch can be detected (Step 802). The jaw patch is the continuous smooth part of buccal side of gums and teeth and can be automatically detected. Advantageously, based on jaw patch, buccal ridge can also be automatically detected; i.e., the buccal ridge can be detected without requiring a user to manipulate the model.

Figure 10:
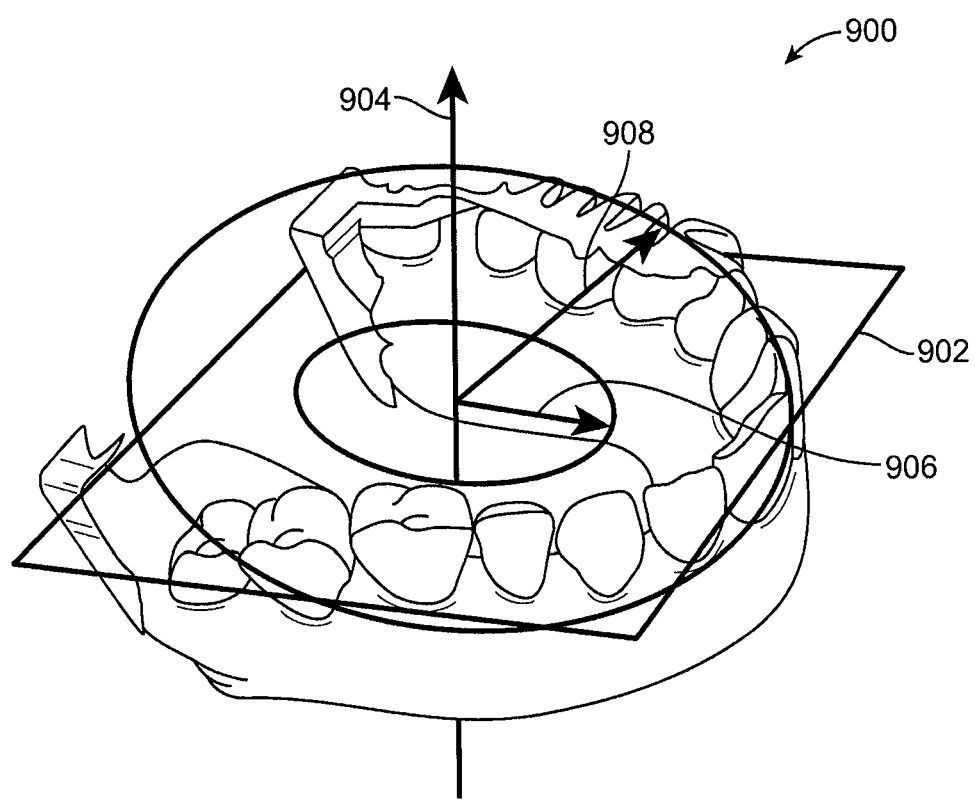
FIG. 10 illustrates a model for jaw patch detection according to an embodiment of the present invention.

In accordance with an embodiment of the present invention, with reference to FIGS. 9 and 10, the jaw patch can be detected (Step 802) via the following routine:
1. Compute the middle plane 902 of the model 900, where the middle plane 902 is the average plane of all vertices in the model 900.
2. Determine the centre Z axis 904 of the model 900, where the centre Z axis 904 passes through the centre of the model 900 and is normal to the middle plane 902.
3. Mark jaw vertices v, by isolating the vertices v where:
    a. A distance from v to the centre Z-axis 904 is bigger than R1 906 and smaller than R2 908, where R1 906 is the radius from the center Z-axis 904 to an innermost vertex of the model 900 and R2 908 is the radius from the center Z-axis 904 to an outermost vertex of the model 900.
    b. A norm to the model 900 at vertex v makes an angle with the centre Z-axis 904 not less 45 degrees.
4. Segment the jaw model into "smooth patches" by following "region growing" algorithm:
    a. Assign all "jaw vertices" with a patch number 0, means it is not checked.
    b. Select one "jaw vertex" from the jaw model that not "checked" yet (patch number equals 0). Assign the vertex with a new patch number bigger than 0. Create a variable length array to store vertices of the patch (called patch array), and put this jaw vertex in the array as the first element.
    c. Get one vertex from the patch, check all of its neighbor vertices:
        i. If the neighbor vertex is already marked (patch number not equal 0), go to next neighbor vertex.
        ii. Else if the neighbor vertex is close to current vertex, i.e., the direction of neighbor vertex is close to current vertex's direction, it is marked as current patch number and put into patch array.
        iii. Else go to next neighbor vertex.
    d. Repeat (c.) until all vertices in the patch array are processed.
    e. Increase the patch number by 1. Repeat (b.), until all "jaw vertices" in the model are processed.
5. Choose the largest patch of the "smooth patches" detected. Slightly grow it bigger to merge other smaller "smooth patches"
6. The merged largest patch is then the "jaw patch".

Figure 11:
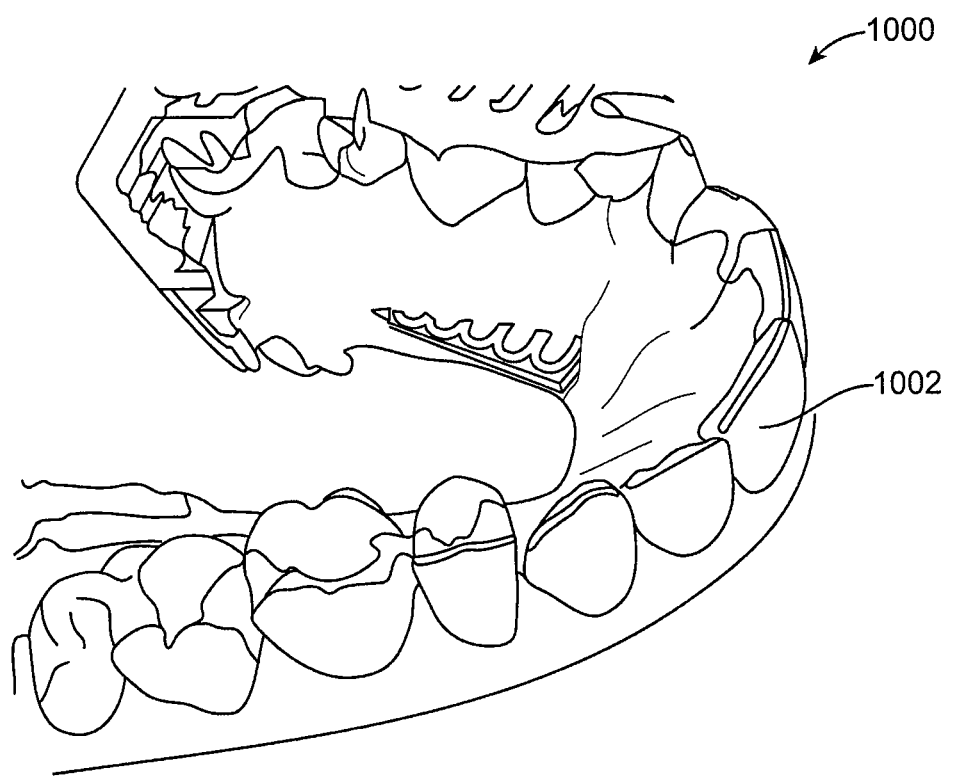
FIG. 11 illustrates a model for which a jaw patch has been detected according to an embodiment of the present invention.

FIG. 11 illustrates a model 1000 for which a jaw patch 1002 has been detected in accordance with the aforementioned routine.

Figure 12:
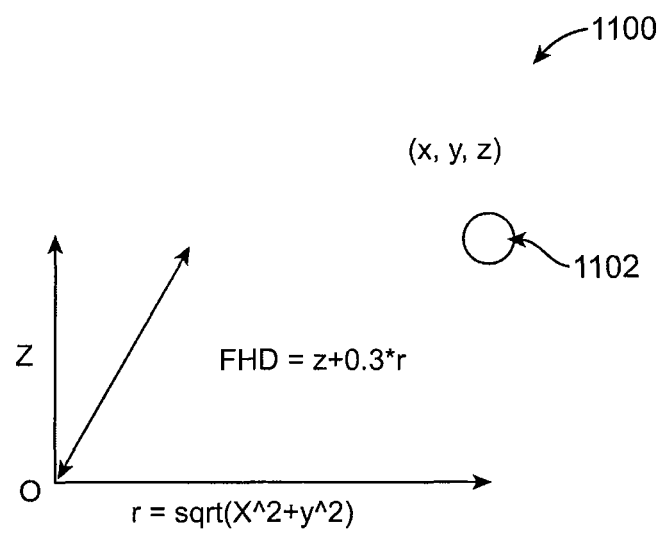
FIG. 12 illustrates a spatial representation for calculating FHD according to an embodiment of the present invention.

In accordance with an embodiment of the present invention, buccal ridge points for the treatment and planning models can be detected (Step 804). In the case that at least one of the models includes teeth not segmented from the jaw, Step 804 follows Step 802. In the case that none of the models included teeth not segmented from the jaw, Step 802 is unnecessary. For planning model, where teeth are segmented, the buccal ridge points can be detected tooth by tooth. The buccal ridge of the jaw can be formed by all the buccal ridge points of all teeth. For tracking model, the buccal ridges points are detected against the jaw patch (e.g., as described above). Accordingly, the points on the buccal ridge are high in the Z-direction and far in the buccal direction (i.e., the buccal ridge points are located in an uppermost and outermost area of the tooth or jaw patch). To identify the points on the buccal ridge, the far-high distance (FHD) of a point to the Z axis is calculated for each vertex as:

$$FHD = z + w_r \cdot r \qquad (10)$$

Where z is the distance along the Z axis, r is the distance to the Z axis, and $w_r$ is the weight of the radial direction. FIG. 12 illustrates a spatial representation 1100 of the relationship between z, r and FHD for a point 1102. The value of $w_r$ is normally less than 1.0 and bigger than 0 and may vary tooth by tooth. For anterior teeth like canine and incisor, $w_r$ can be 0.1 to 0.7. For posterior teeth like premolar and molar, $w_r$ can be 0.4 to 0.8. For tracking model, where only jaw patch is used, $w_r$ can be 0.2 to 0.8.

Figure 13A:
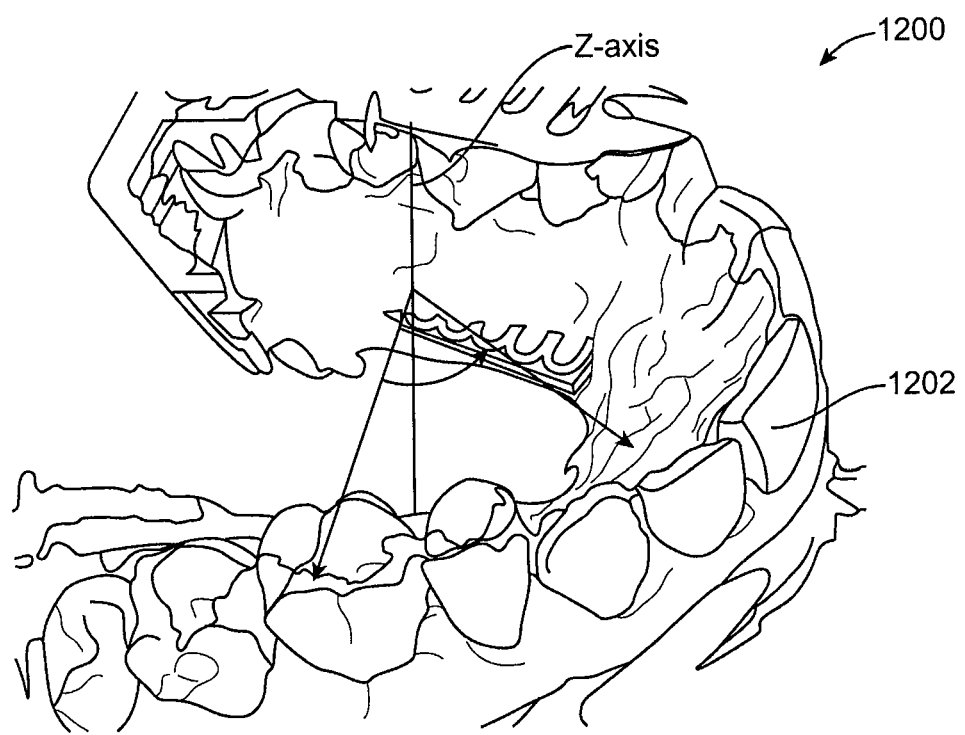
FIG. 13A illustrates a tracking model for which buccal ridge points have been detected according to an embodiment of the present invention.
Figure 13B:
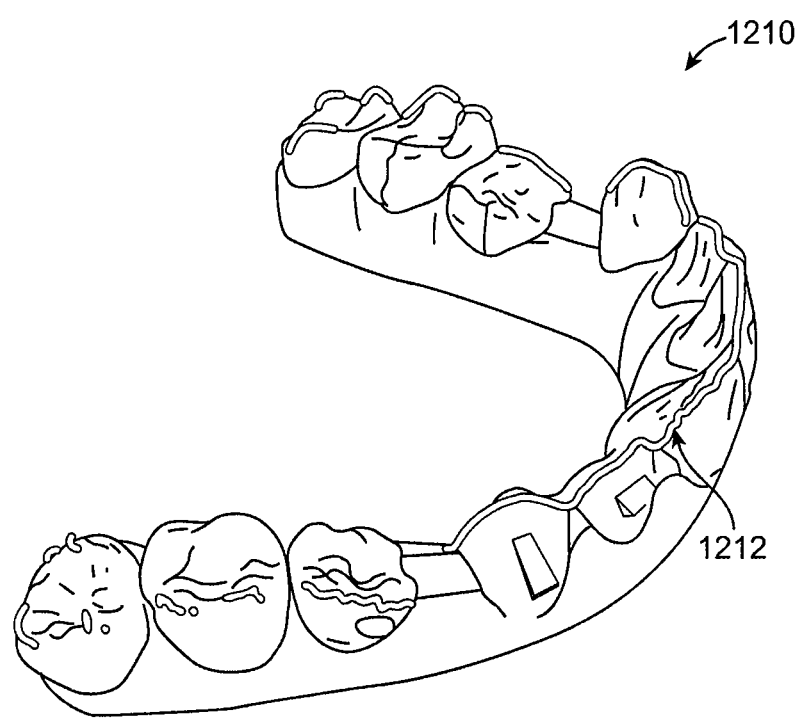
FIG. 13B illustrates a planning model for which buccal ridge points have been detected according to an embodiment of the present invention.

The buccal ridge points of a model can then be found as the points having the maximal FHD in each radial cross section of the model. FIG. 13A illustrates a tracking model 1200 for which buccal ridge points 1202 have been detected. FIG. 13B illustrates a planning model 1210 for which buccal ridge points 1212 have been detected.

After the buccal ridge points are found, a buccal ridge ellipse can be formed (Step 806) for the models. The buccal ridge ellipse can be formed by the following algorithm:

1. Find the occlusal plane from all detected buccal ridge points by Random Sample Consensus (RANSAC) algorithm, which can find a plane that fit most detected buccal ridge points.
2. Project the buccal ridge points into the occlusal plane to form a two-dimensional array as:

$$(x_i, y_i) i=1,2,\ldots N \quad (11)$$

Where N is the total number of detected buccal ridge points.
3. Assume the points in the two-dimensional array fit the following quadratic equation:

$$a \cdot x^2 + b \cdot xy + c \cdot y^2 + d \cdot x + e \cdot y + f = 0 \quad (12)$$

4. Minimize the error using Singular Value Decomposition (SVD) and get the parameters a, b, c, d, e, and f
5. Check the type of the resulting curve (e.g., ellipse or hyperbola).
6. Find the major axis of the ellipse.

Once the buccal ridge ellipse is formed, an Anterior Middle Point Basis (AMPB) can be generated (Step 808) for the models. The AMPB is defined as follows:

The origin point (O) is at the end of the major axis of the buccal ridge ellipse.
The Z-axis is normal to the occlusal plane.
The Y-axis is tangent to the ellipse at O.
The X-axis is the cross product of Y-axis and the Z-axis.

Figure 14:
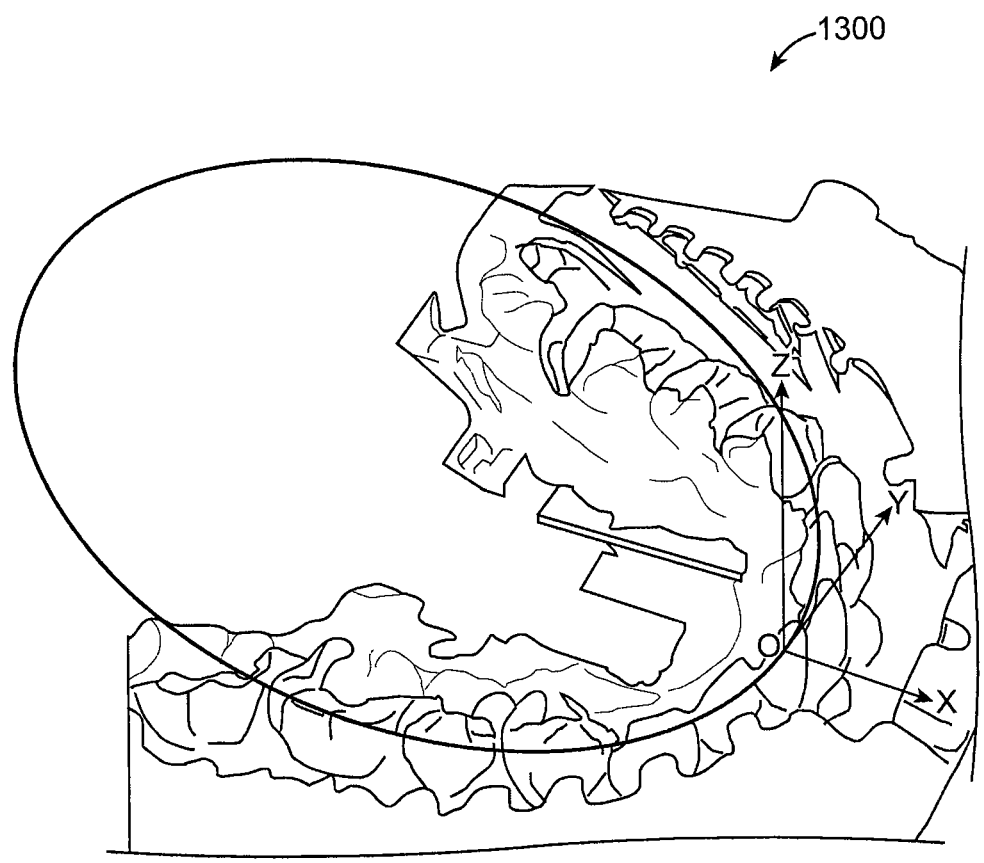
FIG. 14 illustrates a model for which an AMPB has been generated according to an embodiment of the present invention.

FIG. 14 illustrates a model 1300 for which an AMPB has been generated.

After an AMPB has been generated for at least two models (e.g., a tracking model and a planning model), the models can be roughly matched by superimposing their AMPBs onto one another. (Step 810). Given the AMPB of a tracking model as a transform $(R_t, T_t)$ and the AMPB of a planning model as a transform $(R_p, T_p)$, the transformation of the tracking model to the planning model can be defined as $(R_m, T_m)$, where:

$$R_m = R_p \cdot R_t^{-1} \quad (13)$$

$$T_m = T_p - R_m \cdot T_t = T_p - R_p \cdot R_t^{-1} \cdot T_t \quad (14)$$

Fine Matching Models

After two models (e.g., a tracking model and a planning model) are roughly aligned with one another, the two models can be finely aligned with one another and a best match stage can be found (Step 404B). In an exemplary embodiment of the present invention, ICP, as previously described, can be used to finely align the models using vertices of the models as source points for the ICP algorithm. In the case of using vertices of a planning model, in accordance with an embodiment of the present invention, the vertices only include vertices of a crown part of the teeth. Other parts, including root and interproximal areas of the teeth, can be inferred from the crown part and may be modified by an operator. Also, root areas of the teeth are not normally capture by tracking model. Therefore, in an exemplary embodiment, tracking and planning models may be matched using only crown vertices.

In an embodiment of the present invention, a plurality of planning models can be provided. If treatment is performed in accordance with the Invisalign® System, at least theoretically, the tracking model should fit one of the plurality of planning models. This one planning model can be referred to as the "best matching stage." To find this "best matching stage," matching between the tracking model and each of the plurality of planning models can be performed. Various techniques can then be employed to determine and compare the quality of the matches so as to determine which of the plurality of planning stages the tracking model has a closest match with. For example, the ratio of the matched vertices (i.e., the vertices that are not outliers) to the total number of vertices can be used to find the best match stage.

Fine Matching Individual Teeth

After fine matching of models is performed and a best match stage is found, each individual tooth of the planning model corresponding to the best matching stage (or of the only planning model in the case that there is only one planning model) can be matched to the individual teeth of the tracking model (Step 404C). Since the two models should already be well aligned due to the previous rough and fine alignment steps, each tooth in the tracking model should already be close to its correct position. As previously described, the matching of individual teeth can be performed using matching algorithms such as surface matching, feature matching, and the like. In an exemplary embodiment, ICP is used to match the finely teeth of the models to one another, where teeth vertexes are used by the ICP algorithm.

After tooth matching, teeth are repositioned to the tracking model. The tooth position in the tracking model is then computed (Step 404C). Basically, a purpose of matching algorithm (rough matching and ICP matching) is to compute the transformation (movement) between two model. So, in step 404C, the tooth is moved from it's original position in planning model into position in the tracking model.

According to an embodiment of the present invention, the quality of tooth matching can be evaluated. To evaluate the quality of tooth matching, two matching ratios for each tooth can be defined. A "best matching ratio" (MR1) can be defined as:

$$MR1 = \frac{\text{Number of vertices with error} < 0.1 \text{ mm}}{\text{Total vertices in crown}} \quad (15)$$

A "good matching ratio" (MR2) can be defined as:

$$MR2 = \frac{\text{Number of vertices with error} < 0.2 \text{ mm}}{\text{Total vertices in crown}} \quad (16)$$

Usually, the displacement error of a vertex is in the best matching ratio if it is due to random noise, such as that introduced by scanning the patient's teeth to acquire a model. Error in the good matching ratio may come from slight model distortion due to digital detailing (DDT) when teeth are segmented in an impression model using, for example, ToothShaper software. Vertices that are not in the good matching ratio are usually due to the presence of erroneous extra material provided in, for example, an impression or attachment.

The tooth matching ratio can also be used to check the quality of an impression. Table 1 illustrates common sources of error for various matching ratios.

TABLE 1

| MR2 Matching Ratio (<0.2 mm) | MR1 Matching Ratio (<0.1 mm) | | |
|---|---|---|---|
| | 0-0.4 | 0.4-0.6 | 0.6-1.0 |
| 0-0.4 | Failed matching | N/A | N/A |
| 0.4-0.6 | Bad impression quality | Low impression quality | N/A |
| 0.6-1.0 | N/A | Extra material or attachment | Good impression and matching |

Tooth Movement Measurement by Stationary Teeth

As a result of the matching step 404, the positions of the teeth in the tracking model can be determined. In an embodiment of the present invention, these positions can then be used for a final re-alignment of the models that takes into consideration intended and/or actual movement of the teeth. Such realignment can subsequently be used to measure movements in the positions in teeth of a model.

Two models (e.g., a tracking model and a "best match" planning model) can be re-aligned by detecting stationary or near-stationary elements (Step 406). The stationary or near-stationary elements may include teeth, regions beyond tooth crowns, and the like. In orthodontic treatment, in general, every tooth is moving. So, there is no absolutely stationary tooth. However, from the treatment plan, it is possible to find the teeth which are not supposed to be moved in accordance with the treatment plan. These teeth can be considered to be stationary and can thus be used as reference for measurements of other teeth movement. Accordingly, re-alignment of the models can be performed by minimizing the cost function of the weighted displacement error between the planned jaw position (i.e., planning model or treatment model) and achieved jaw position (i.e., tracking model), the cost function being defined as:

$$J = \sum_{i=1}^{N} \sum_{j=1}^{M} \|w_1 \cdot (R^s(R_i^P P_{i,j} + T_i^P) + T^S - (R_i^t P_{i,j} + T_i^t)\|^2 \quad (17)$$

Where, $P_{i,j}$ is the position of vertex j in tooth i; $(R_i^t, T_i^t)$ is the position of the teeth in the tracking model; $(R_i^P, T_i^P)$ is the position of the teeth in the planning model; $(R_i^s, T_i^s)$ is the relative position of stationary teeth; N is the total number of teeth in the models; and M is the total number of vertexes for each tooth in the models.

In an embodiment of the present invention, the weight $w_i$ of each tooth i can be determined based on the planned tooth movement for a certain stage. Less moved tooth should be more stationary and with bigger weight. The weight for tooth with large movement should be small or equal 0. In accordance with this embodiment, first, for each vertex in the crown, the following move distances are computed:

Rotation distance RD. For a vertex in the tooth, the displacement vector is defined as the vector of the vertex from tooth initial position to the planning position. This displacement vector is projected on the plane perpendicular to the Z-axis and then onto the line perpendicular to the radius; i.e., the rotation distance around the Z axis of tooth (or the incisal—gingival direction).

Tip distance TD, is defined as the movement perpendicular to the vector from the vertex to the root centre in the plane of this vector and the Z-axis.

Intrusion distance ID and extrusion distance ED, the outward and inward movement from/to the root in the Z-direction, respectively.

Figure 15:
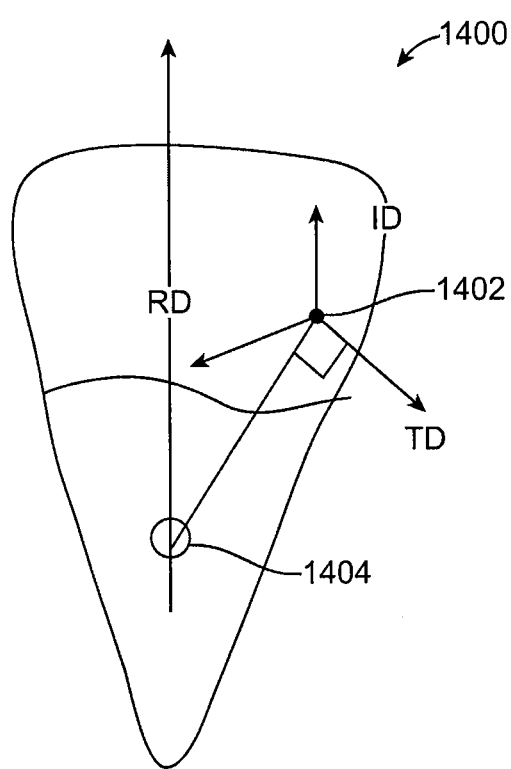
FIG. 15 illustrates a tooth and associated movement vertices according to an embodiment of the present invention.

FIG. 15 illustrates a tooth 1400 and an associated vertex 1402, the associated root 1404, and the relationship between the vertex 1402, root 1404, RD, TD, and ID, where ED is in a direction opposite the direction of ID.

The maximum of RD, TD, ID and ED (i.e., "Max RD", "Max_TD", etc.) can be found over all of the vertices in the crown and the weighted sum of the maximal distances ("WMD") can be computed according to the formula:

$$WMD = w_1 Max\_RD + w_2 Max\_TD + w_3 Max\_ID + w_4 Max\_ED \quad (18)$$

Where $w_1$-$w_4$ are weights that are different for different types of teeth and are based on the difficulty of each type of movement and tooth size. For molar and premolar, all movement are difficult, so the weights are bigger. For canine, the extrusion and rotation movements are difficult, so $w_1$, $w_4$ are bigger. In an embodiment of the present invention, the WMD can be limited to be between 0.1 and 2.

Using the WMD, the weight of one tooth movement can be computed as:

$$w = 0.1042105/WMD - 0.042105 \quad (19)$$

So that when WMD=0.1, w=1; when WMD=2, w=0.01. i.e., if tooth movement is bigger, the weight is almost 0.

In accordance with using equation (19) to calculate the weight of each tooth, for WMD=2.0, or maximum movement, the weight w will be 0.01; for WMD=0.1, or almost no movement, w=1.0; which means that teeth planned to move slower contribute more in equation (17) and teeth planned to move faster contribute less to equation (17). Accordingly, the stationary position ($R^s$, $T^s$) depends more on slowly moving teeth than on faster moving teeth. Accordingly, stationary (and near stationary) teeth can be detected.

In another embodiment of the present invention, the weight $w_i$ of each tooth i can be determined based on the de facto immobility of the teeth, since actual movement of teeth may be very different from planned movements. Consequently, information regarding which teeth are stationary (or nearly stationary) may be inferred only by comparing the tracking model with the planning models. Accordingly, one method for calculating the weight of each tooth includes:

1. Assigning the weights for all teeth to 1.
2. For every pair of teeth T1 and T2 in an original or previous tracking model, computing a transformation $L_{init}$.
3. For every pair of teeth T1 and T2 in a most recent or current tracking model, computing a transformation $L_{curr}$.
4. For every vertex v of tooth T1 compute the distance $D_v$, between $L_{init}(v)$ and $L_{curr}(V)$, i.e., compute the difference between the results of application of the transformations $L_{init}$ and $L_{curr}$ to the vertex v.
5. Determining the maximum number D of all numbers $D_v$; i.e., determine the maximum D over all vertices of tooth T1.
6. If D is less than a predefined tolerance, $\epsilon$, then increasing the weight for tooth T1 by 1. A preferred value for $\epsilon$ is 0.2 mm.
7. Repeating steps 2 to 6 for all pairs of teeth in the same model.
8. Dividing the weight of each tooth by the sum of all weights of the teeth in the same model.

This method automatically assigns bigger weights to the teeth that move the least amount, thus advantageously detecting stationary (and near stationary) teeth.

In an embodiment of the present invention, the resulting weights assigned to equation (17) can be the average of the weights derived by equation (19) and the weights derived according to the aforementioned method steps 1 to 8.

Once the tracking model and a planning model are re-aligned based on stationary and/or near stationary elements, planned tooth positions can be compared with actually achieved tooth positions (Step 408) so as to detect one or more positional differences between the actual and planned arrangements of the patient's teeth. Such a comparison can include building up an occlusal plane and archform as a measurement reference (Step 408A) and computing tooth movements relative to this measurement reference (Step 408B). Using an occlusal plane and archform formed from a model that has been re-aligned based on stationary and/or near stationary elements advantageously assures an accurate measurement of positional differences.

In orthodontics, the archform is a smooth curve that roughly passes through some feature points of a dental arch. It describes the arch shape and is important for tooth movement measurement. For example, the mesial-distal movement is the movement in a direction tangent to the archform. The occlusal plane defines the direction of intrusion-extrusion movement of a tooth.

Figure 16:
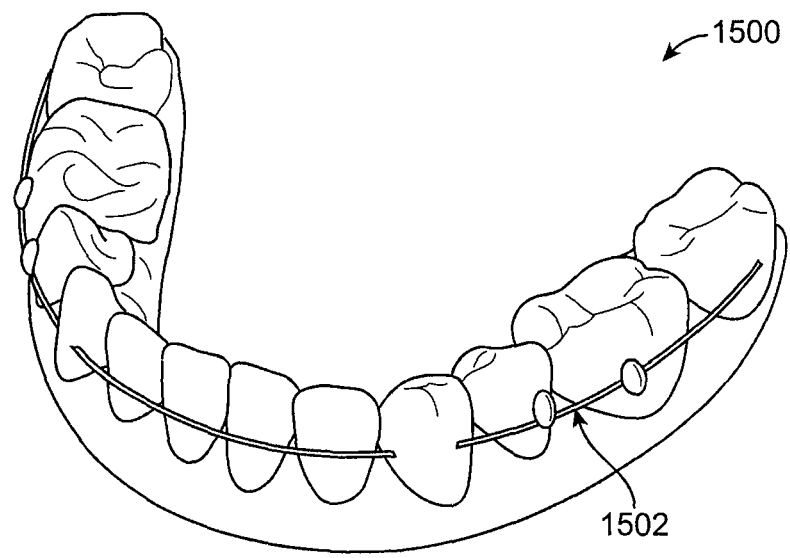
FIG. 16 illustrates a model for which an archform has been constructed according to an embodiment of the present invention.

In an embodiment of the present invention, an archform can be constructed (Step 408A) as a curve based on any of the points on the teeth in a model. In a preferred embodiment, the archform is constructed as a two-segment cubic curve using the facial axis points of all teeth in the tracking model. Similarly, the occlusal plane can be constructed (Step 408A) based on any of the points on the teeth in a model. In a preferred embodiment, the occlusal plane is built by best fitting a plane from the crown centers of all teeth in the tracking model. FIG. 16 illustrates a model 1500 for which an archform 1502 has been constructed as a two-segment cubic curve using the facial axis points of all of the teeth in the model 1500.

After the archform and occlusal plane are constructed, an archform basis can be constructed for each tooth for subsequent calculation of tooth movements. The archform basis can be constructed in accordance with the following definition:

The origin (0) of the basis is the closest point on the archform to the centre of the crown.
The Z-axis is normal to the occlusal plane.
The Y-axis is the tangent to the archform that is projected onto the occlusal plane.

Figure 17:
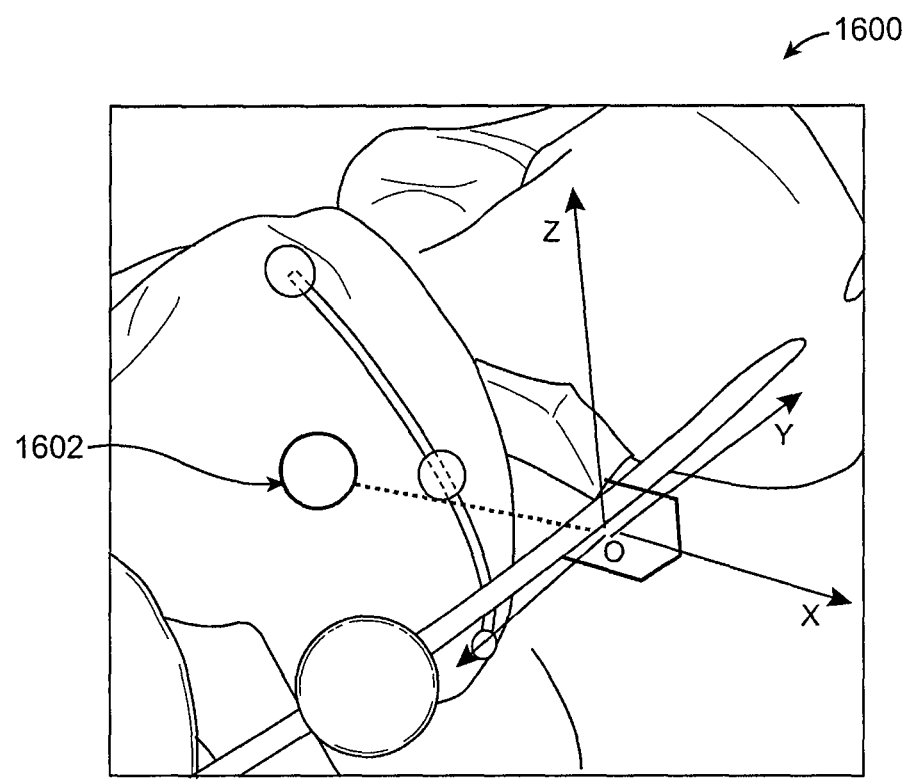
FIG. 17 illustrates a model for which an archform basis for a crown center has been constructed according to an embodiment of the present invention.

FIG. 17 illustrates a model 1600 for which an archform basis for a crown center 1602 has been constructed.

Once the archform basis is constructed, the tooth movement can be computed relative to this basis (Step 408B). In an embodiment of the present invention, the tooth movement can be computed via translation movements and rotation parameters. For example, the tooth movement M with respect to an archform basis can be computed as:

$$M = [R^b]^{-1} R_i P + T_i - (R_0 P + T_0))  \qquad (20)$$

Where P is the position of a vertex in the tooth of the treatment model, $(R_0, T_0)$ is the tooth position at an initial stage (e.g., an original or previous tracking model), $(R_i, T_i)$ is the tooth position at a current stage (e.g., a most recent or current tracking model), and $(R^b, T^b)$ is the transform representing archform basis.

In an embodiment of the present invention, equation (20) can be used to compute the movement of a crown center and root center. In an embodiment of the present invention, the rotation movement of a tooth can be decomposed into inclination, angulation and rotation, or the rotation angle around Y axis, X axis and Z axis by Euler decomposition method. In an embodiment of the present invention, for each planning model, the planned movement and achieved movements are computed based on the planned tooth positions from the planning models and the achieved tooth positions from the tracking model.

Figure 18:
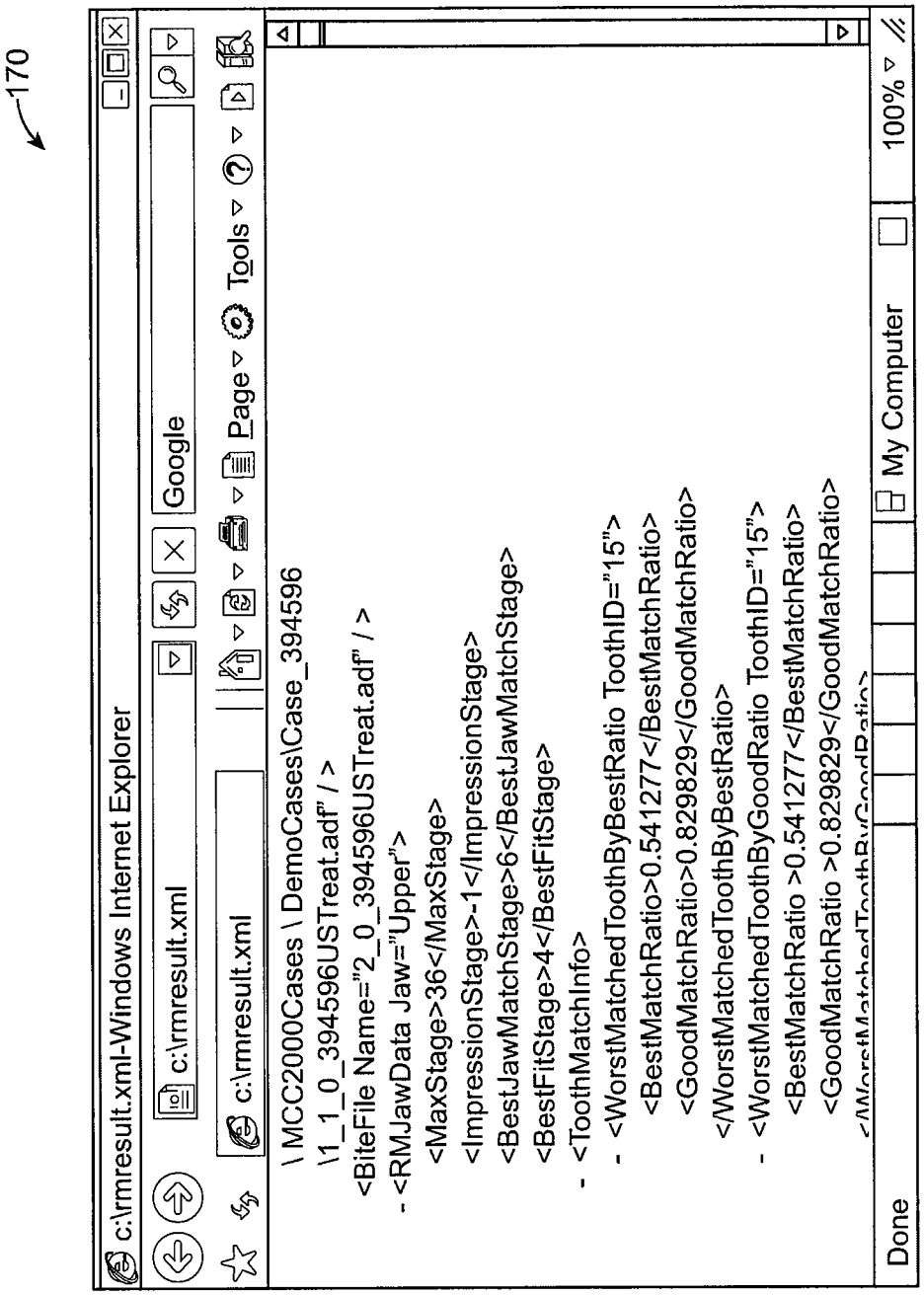
FIG. 18 illustrates an XML output according to an embodiment of the present invention.

In an embodiment of the present invention, the measurement results, including matching quality, can be output. The output can be used for future applications, like date analysis, treatment monitor. The output can be provided in XML format, for example. FIG. 18 illustrates an XML output 1700 in accordance with an embodiment of the present invention.

Utilize Partial Surface as Alignment Reference

In order to evaluate the outcome of a treatment, two models can first be aligned with one another. After the alignment, tooth movements can be compared with their initial positions, and the deviation between planned tooth positions and achieved tooth positions can be calculated. Theoretically, the planned static teeth can be utilized as the references for the model alignment. However, in the actual treatment, it is possible that all of the teeth are planned to be moved. It is also possible that although some teeth are not planned to be moved, they are nonetheless moved during the actual treatment. For example, unplanned movement may result from the aligners being worn since the specific interaction between the aligners and the teeth may be unknown. After the aligners are worn on the teeth, each individual tooth's movement may be unpredictable. Consequently, teeth that are planned to not move may in reality actually be moved. So, in order to more accurately evaluate the absolute deviation, a static reference can be utilized for aligning two models.

In accordance with an embodiment of the present invention, partial regions beyond the tooth crown are used as references to align at least two models; for example, a tracking model and a planning model. When a doctor takes an impression from the patients teeth (or acquires a digital model of the patients teeth using other methods previously described, such as scan techniques), not only are the teeth crowns shape captured, but also the whole arch shape, including gingiva shape, palatine rugae, hard plate, and so forth, are captured. These regions are all located beyond the teeth crowns. The static region can be located in any or all of these regions.

Figure 19:
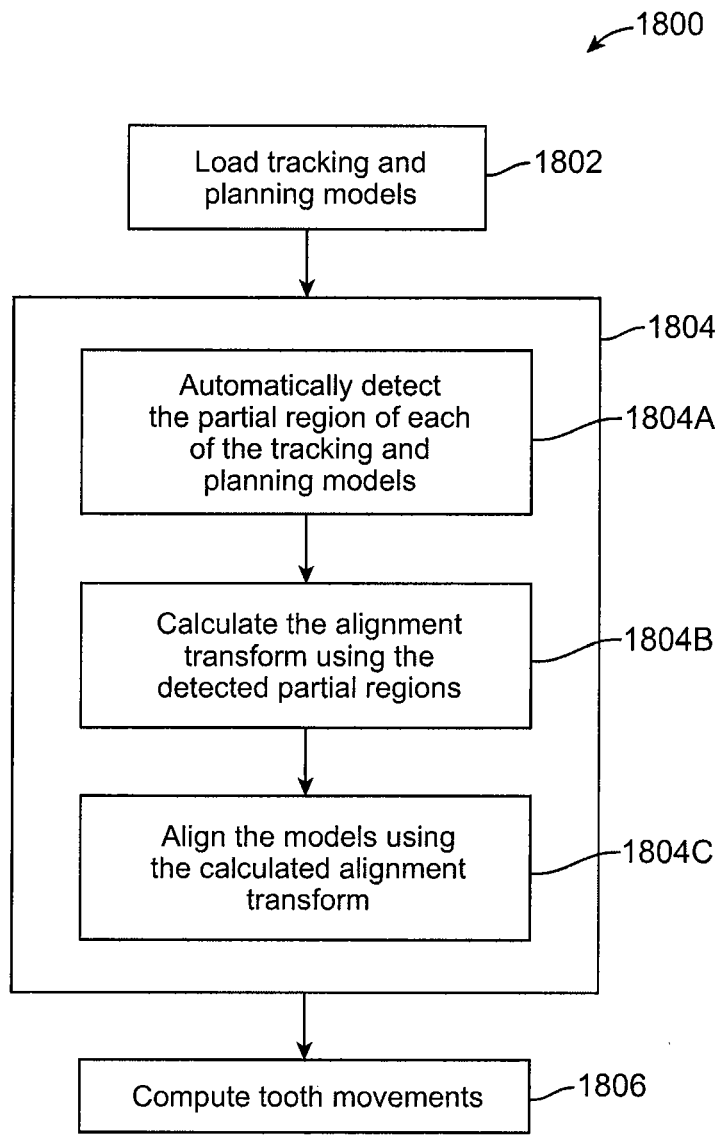
FIG. 19 shows a process including teeth matching according to another embodiment of the present invention.

FIG. 19 illustrates the general flow of an exemplary process 1800 for aligning two models using a partial region located beyond teeth crowns.

The process 1800 for aligning two models may be used independently of the process 400. As an initial step, two models are received by or loaded into a system for automatic alignment (Step 1802). The two models may include a tracking model and a planning model as previously described. In an exemplary embodiment, the tracking model may be a three-dimensional digital model of a patient's teeth during treatment, and the planning model may be a three-dimensional digital model of the patient's initial teeth arrangement. These models may be acquired using any of the techniques previously described.

After loading the tracking and planning models, an alignment step is performed to align stationary elements of each of the two models with one other (Step 1804). The alignment step 1804 can include automatically detecting a partial region of each of the tracking and planning models (1804A), calculating an alignment transform using the detected partial regions (Step 1804B), and aligning the models using the calculated alignment transform (Step 1804C).

Figure 20:
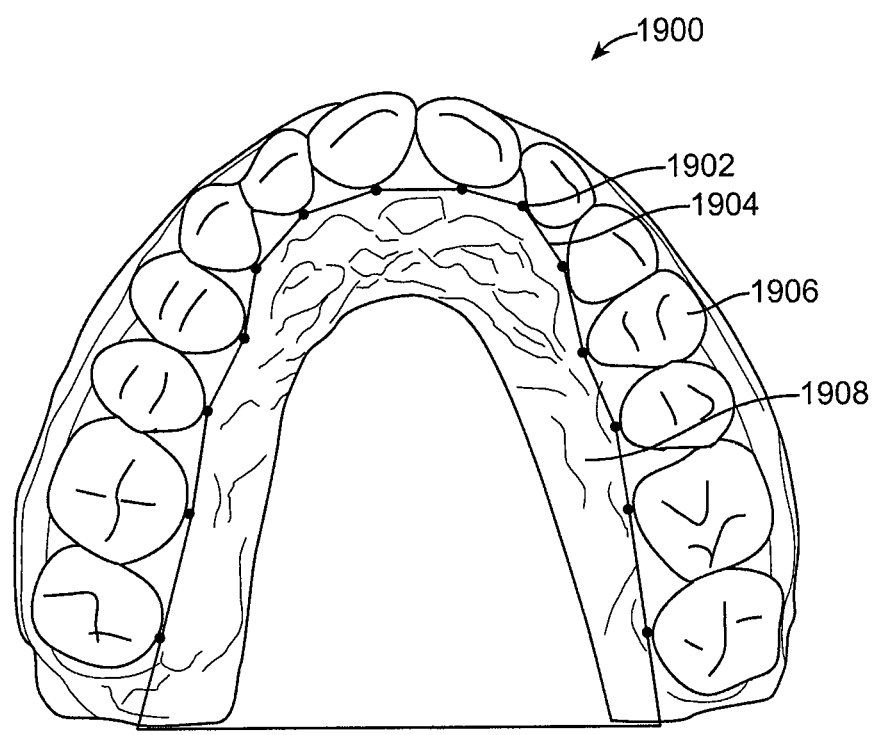
FIG. 20 illustrates a model for detecting partial regions according to an embodiment of the present invention.

The partial region automatically detected in step 1804A could be on the lingual side or buccal side of teeth included in the models. For an upper jaw, the lingual side is preferred over the buccal side since the lingual side comprises the palatine rugae, hard plate, and gingival shape. To utilize the partial region beyond tooth crown as an alignment reference, the partial region need to been automatically detected. In accordance with an embodiment of the present invention, the steps for detecting the partial region may include:

(1) Calculating each tooth's lingual cementoenamel junction (CEJ) point
(2) Connecting the CEJ points in sequence to form a polygon (3) Filtering out the faces which are outside of the polygon (4) After filtering, form the partial region by combining the remaining faces FIG. 20 illustrates a model 1900 for detecting partial regions. The model 1900 includes CEJ points 1902 that have been detected and connected to form a polygon 1904. Faces 1906 are provided outside of the polygon 1904, whereas faces 1908 are provided inside of the polygon 1904. The region inside the polygon including the faces 1908 is the potential static region; this region is assumed to comprise at least one static part.

To calculate the alignment transform, ICP algorithm may be utilized, which has been described previously in "Iterative Closest Point Algorithm". In the implementation, the matching points should be located on the partial surfaces of the planned model and tracking model. By minimizing the error metric in the ICP algorithm, a rigid body transform is obtained as the alignment transform. Then apply the alignment transform to one of the models and make that model moved to the alignment position.

Alternatively, the process 1800 for aligning two models may be used within the process 400. For example, the alignment step 1804 could be used in place of the realignment step 406. In this case, the step of loading the tracking and planning models (Step 1802) is unnecessary since this is performed in step 402. Similarly, the step of computing tooth movements (Step 1806) is unnecessary since this is performed in step 408.

By aligning two models using a partial region beyond tooth crowns, a static region can be captured. Advantageously, the static/absolute partial region can be captured, the static region can be utilized to align two models, and the tooth movements and the deviation (planned vs. actual) can be quantified in a absolute way.

Experimental Results

To test and evaluate the methods of the present invention, 356 middle course correction (MCC) cases were collected and processed. Each cases include one treatment model and one tracking model. Among the 356 cases, there were 297 lower jaws, 336 upper jaws and a total of 8751 teeth.

Figure 21:
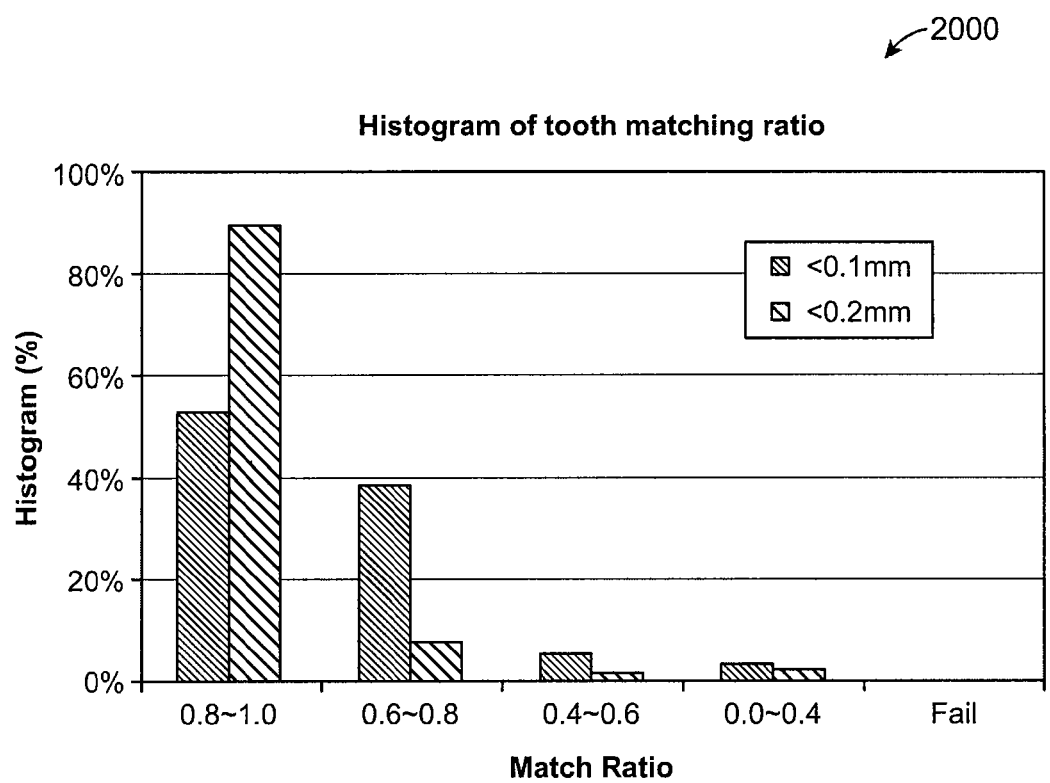
FIG. 21 illustrates a histogram of the matching ratio for all teeth according to an embodiment of the present invention.

FIG. 21 illustrates a histogram 2000 of the matching quality for all teeth. 95% of the teeth are in good matching, and over 50% of the teeth are in best matching. The matching ratios for each are provided on the x-axis, and the percentage of teeth satisfying those matching ratios is provided on the y-axis.

Figure 22A:
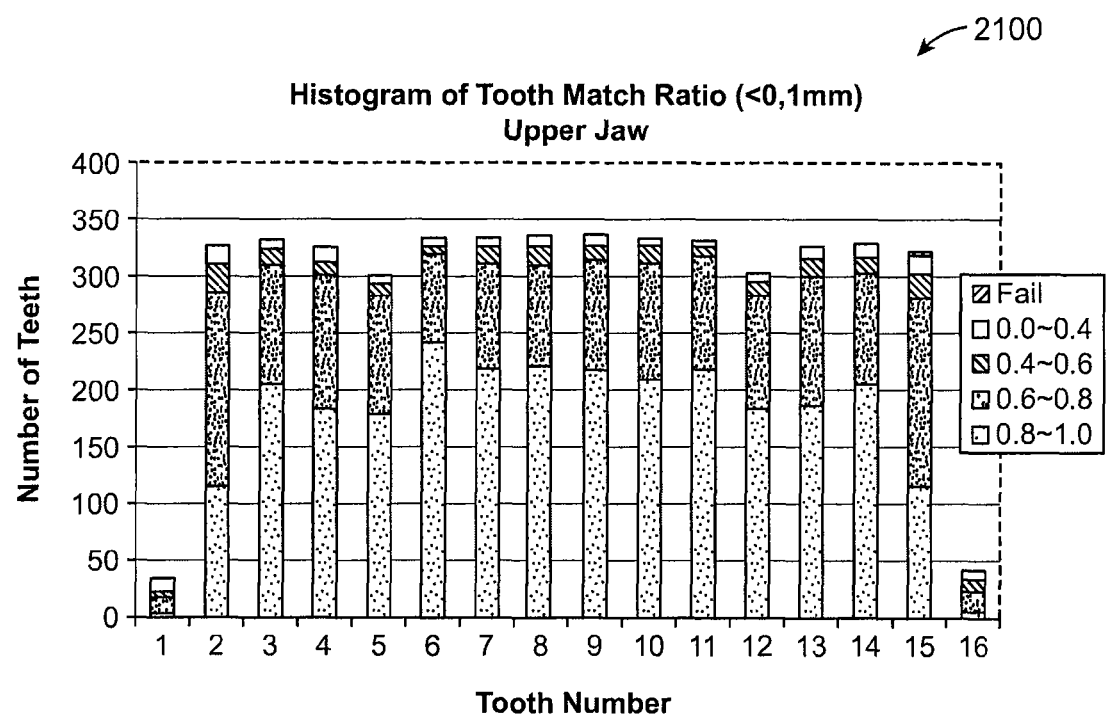
FIG. 22A illustrates a histogram of the number of teeth having matching ratios for individual teeth in an upper jaw according to an embodiment of the present invention.
Figure 22B:
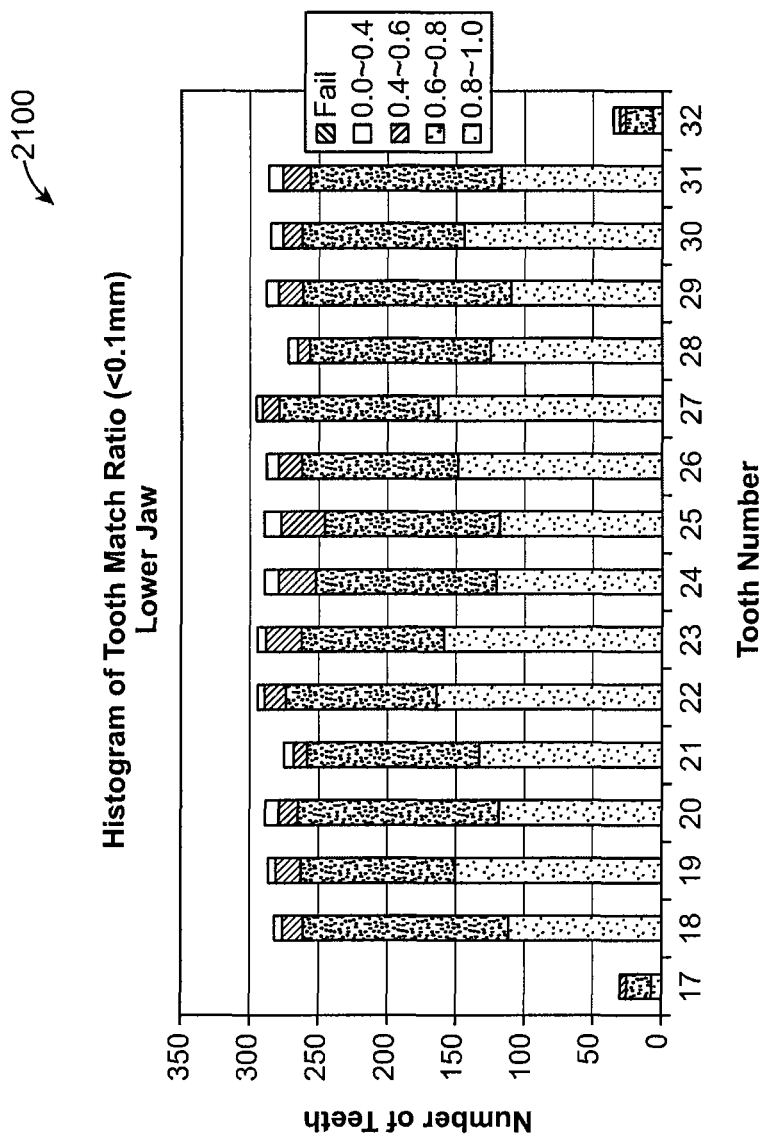
FIG. 22B illustrates a histogram of the number of teeth having matching ratios for individual teeth in a lower jaw according to an embodiment of the present invention.

FIG. 22A illustrates a histogram 2100 of the number of teeth having matching ratios for individual teeth numbers in the upper jaw. The tooth number I provided on the x-axis, where 1, 2, 3 and 14, 15, 16 are molars, 4, 5, 12, 13 are premolars, 6 and 11 are canines, 7-10 are incisors. The number of teeth in each matching ratio is provided on the y-axis. Similarly, FIG. 22b illustrates a histogram 2110 of the number of teeth having matching ratios for individual teeth numbers in the lower jaw.

Figure 23A:
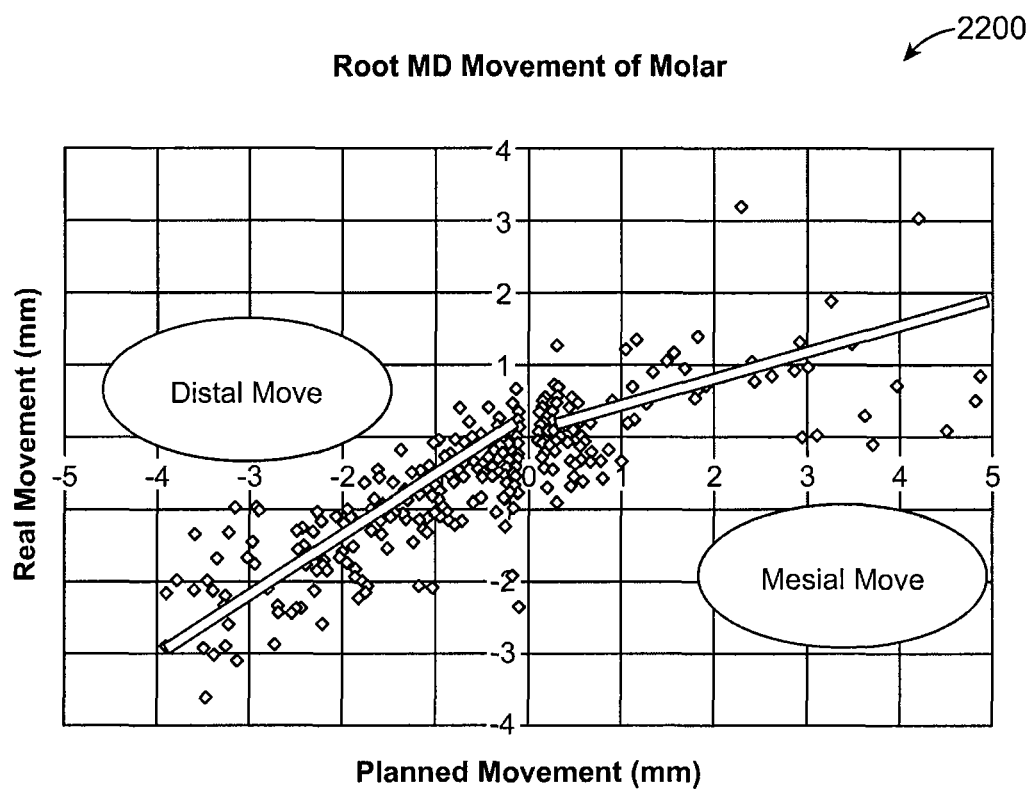
FIG. 23A shows a graph of the mesial-distal movement distribution of the root centers of molars according to an embodiment of the present invention.
Figure 23B:
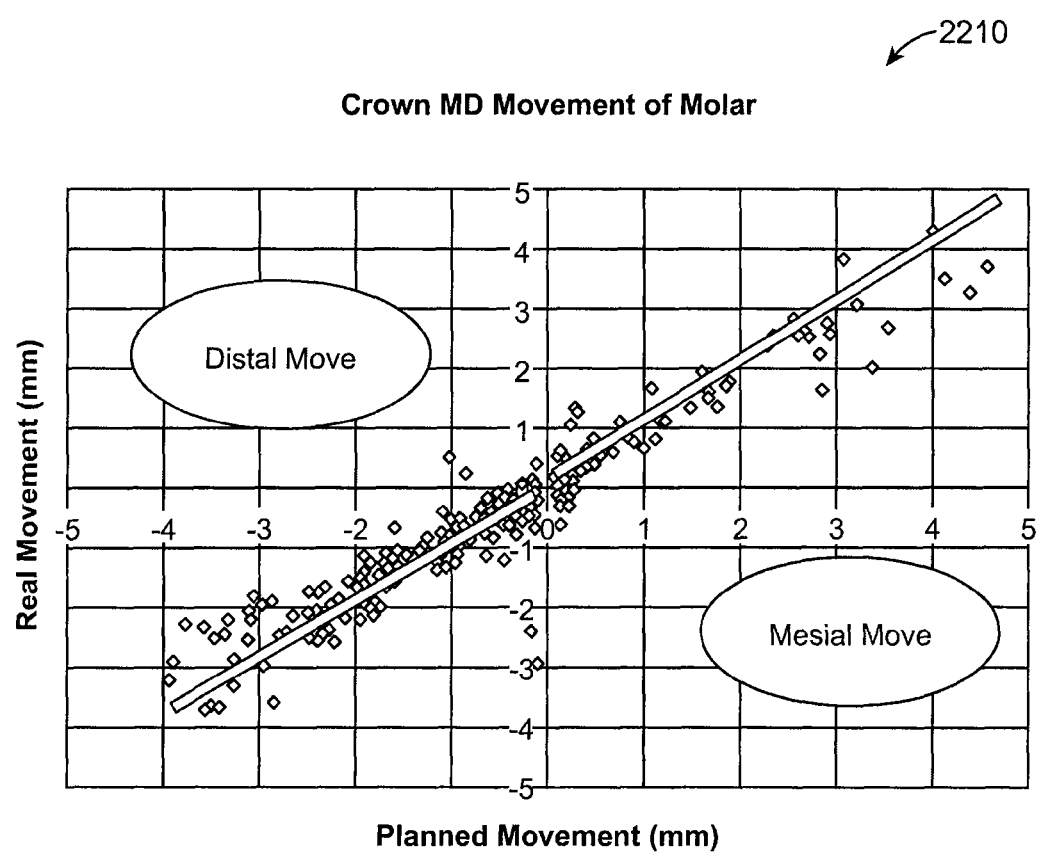
FIG. 23B shows a graph of the mesial-distal movement distribution of the crown centers of molars according to an embodiment of the present invention.

FIG. 23A illustrates a graph 2200 showing the mesial-distal movement distribution of the root centers of molars. The planned movement is on the x-axis (mm) and the real movement is on the y-axis (mm). FIG. 23B illustrates a graph 2210 similarly showing the medial-distal movement for crown centers of molars.

The inventors of the subject application recognized that distal movement of tooth roots is difficult to achieve and less predictable than distal movement of crowns. On average, only 75% of planned movements can be achieved for all kinds of movement. They also recognized that crown movement is more predictable than distance movement and up to 90% of planned movements can be achieved, and that large mesial movements are very unpredictable and only 50% of planned movements can be achieved.

While the timing of the progress tracking steps described herein can be selected by the practitioner, typically at least general timing for conducting progress tracking measures of the present invention will be incorporated into the treatment plan and, therefore, will be pre-planned or planned at about the beginning of treatment or early on in the course of the patient's treatment (e.g., prior to the patient wearing a given set of appliances so as to reposition the teeth). Thus, in one embodiment of the invention, a treatment plan will include a prescribed timing for the planned tracking steps. The prescribed timing can include a specifically recommended date or may include a general increment of time (e.g., at treatment week 9, 10, 11, etc.), or can be based on the timing of other events of the treatment plan (e.g., after a patient wears a set of appliances).

Timing of progress tracking steps can be selected to occur based on a somewhat standardized treatment protocol or can be more particularly customized to an individual patient. More standardized protocols can take into account certain population statistics, generalized clinical expectations, and/or physiological parameters that can be used to generally predict rate of movement of a patient's teeth and the minimum length of treatment time necessary for the patient's teeth to progress off track if such progression is occurring. Clinical parameters can include, for example, root structure, including length, shape, and positioning, as well as certain jaw characteristics such as jaw bone density, patient age, gender, ethnicity, medications/health history profile, dental history including prior treatment with orthodontics, type of orthodontic treatment plan (extraction vs. non-extraction), and the like. Assuming a 2-week wear interval for each appliance, with a maximum tooth velocity of 0.25 mm/tooth per aligner, typically about 16 to 20 weeks of repositioning treatment (8 to 10 appliances) is required before movement of the teeth is substantial enough to detect a noncompliant or off track movement of the teeth, if such off track movement is occurring, though more drastic movements can produce off track movement after only a few weeks.

As set forth above, timing of tracking measures can be selected based on the particular movement(s) prescribed and/or characteristics of the patient being treated and, therefore, are said to be customized to the particular patient. For example, certain desired tooth movements in a treatment plan may be deemed either more unpredictable or at increased risk of moving off track and may require specifically timed tracking or monitoring. For example, for certain movements including, e.g., extrusions or rotations of round teeth (e.g., canines), more specific or frequent tracking may be desired. Additionally, certain physiological or clinical characteristics of the patient may be identified as indicating that particularly timed and/or frequency of tracking might be desired. Whether tracking is selected based on standardized protocols or more customized to the individual patient, tracking may or may not be selected to uniformly timed during the course of treatment. For example, a lower frequency of tracking measures may be desired or needed during certain portions or phases of treatment than others (e.g., space closure). Regardless of whether tracking timing is customized or more standardized, the selected timing will typically provide the additional advantage of efficiently planning tracking in the treatment plan to minimize unnecessary use of practitioner time and other resources.

Figure 24A:
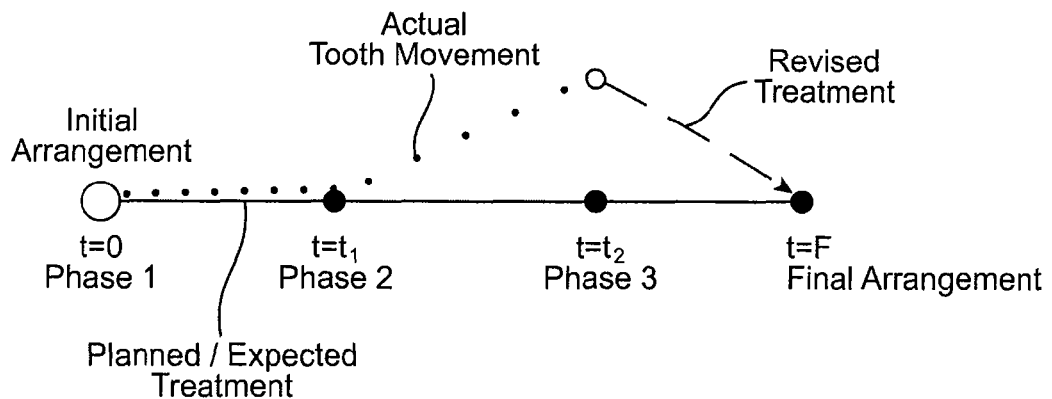
FIG. 24A through FIG. 24C show plurality of stages of teeth correction and revision of treatment, according to several embodiments of the present invention.
Figure 24B:
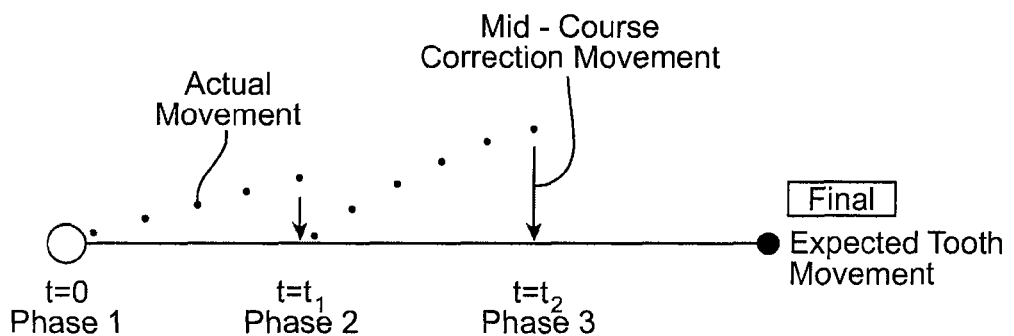
Figure 24C:
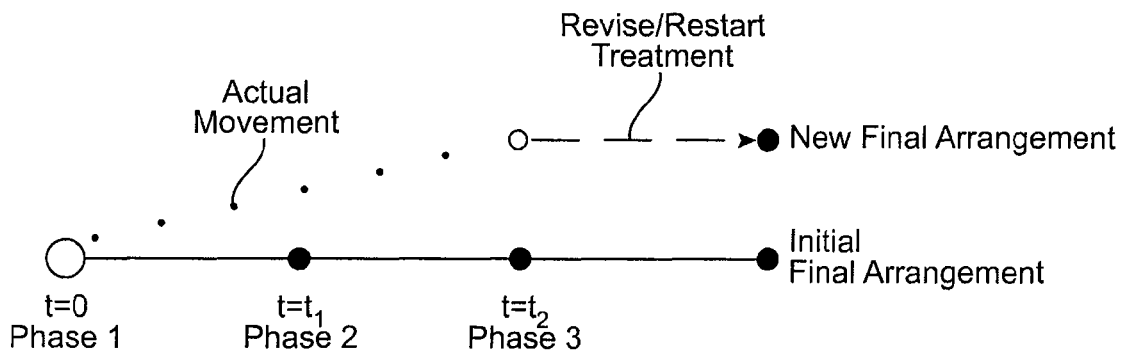

Once a determination is made that the patient's actual arrangement of teeth deviates from a planned arrangement and that the patient's teeth are not progressing as expected/planned, a change or correction in the course of treatment can be selected, for example, by generating a revised or modified treatment plan. Referring to FIGS. 24A-24C, revised treatment following determination that a patient's teeth are not progressing on track is described. As set forth above, a treatment plan includes a plurality of planned successive tooth arrangements for moving teeth along a treatment path from an initial arrangement to a selected final arrangement. The treatment plan, administration of sets of appliances to a patient according to the planned arrangements, can include a plurality of phases (1 through 4) where at time=0, the initial treatment plan begins. The initial treatment plan is illustrated by a solid line. Matching for a determination of whether a case is progressing "on track" or "off track", as described above (e.g., FIG. 3), can take place at one or more of the phases or points along the administration of treatment.

In particular, current tooth positions of the patient can be obtained from the patient at any one or more phases and compared to segmented models of the patient's teeth according to an earlier or original treatment plan. Where teeth are determined to be deviating from the planned treatment plan or progressing "off track", as illustrated by broken lines, modification or revision of treatment plan can occur. In one embodiment, a revised treatment plan can include restaging the patient's treatment from the determined actual position to the originally determined final position (FIG. 24A). Revised treatment path (illustrated by dashed lines) can proceed directly toward the initially determined final position and need not attempt to redirect treatment back onto the original treatment path. In this case, while partial overlap/intersection of the revised treatment path with the original treatment path may occur, the revised treatment path will at least partially diverge from the initial treatment path and proceed directly toward the initially determined final arrangement of the teeth. Such an approach may be selected, for example, where retaining the initially determined final position is desired. This approach also advantageously permits use of the originally processed and segmented data, thereby allowing avoidance of costly processing steps.

Alternatively, a revised treatment plan can include a more direct "mid-course correction", in which the revised treatment plan includes a more direct path back toward the a planned arrangement of the initial treatment plan, as illustrated in FIG. 24B. While this approach may make use of the originally planned final arrangement, the more primary concern in this example type of correction is redirecting treatment back to the original treatment path, rather than from the actual position and more directly toward the original final position. In yet another embodiment, as illustrated in FIG. 9C, a revised treatment plan can include essentially "re-starting" treatment, and generating a new final arrangement of the teeth, for example, from segmenting and staging a new impression of the teeth, and directing the patient's teeth from the actual arrangement to the newly determined final arrangement of the teeth.

Figure 25:
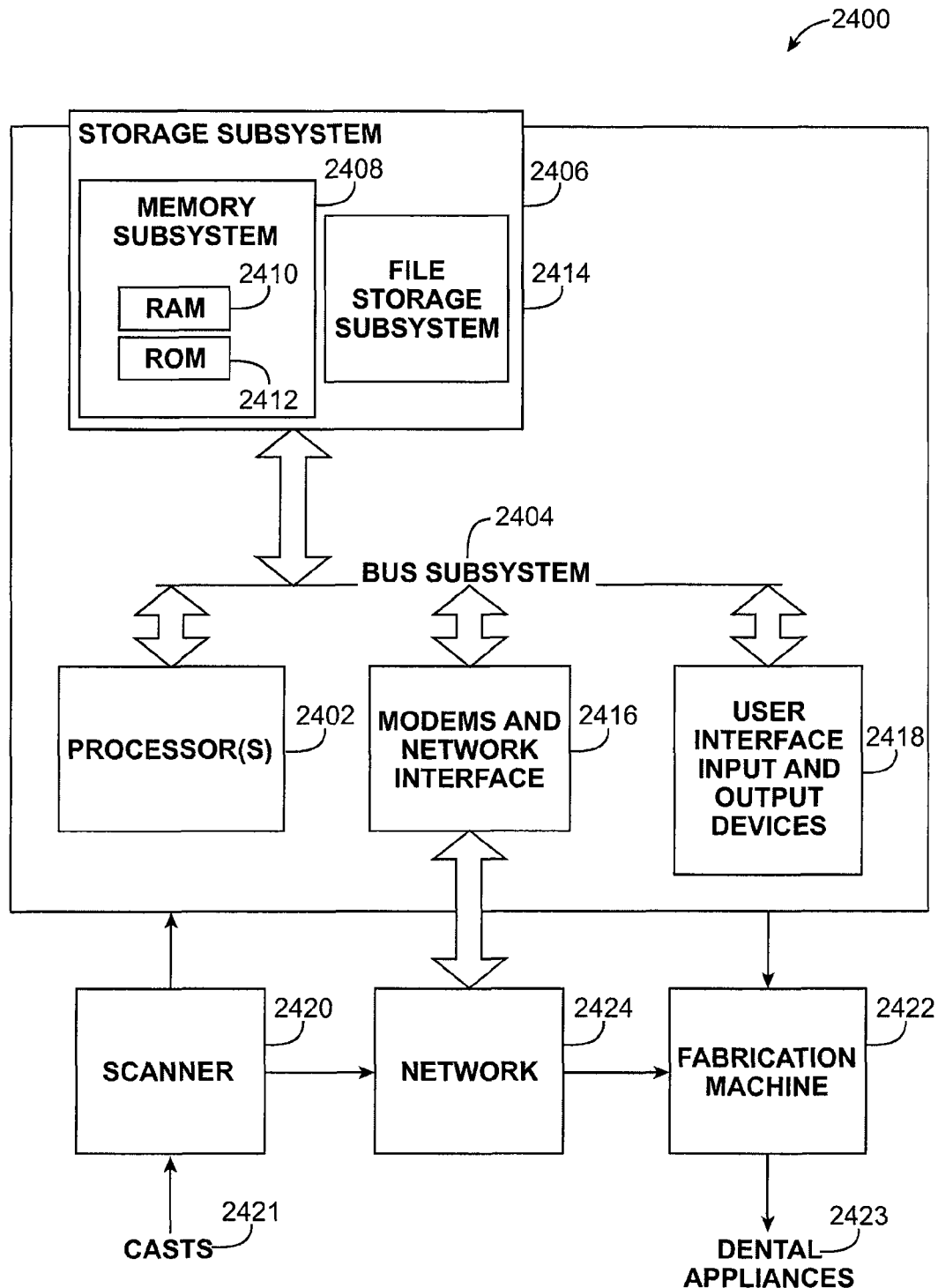
FIG. 25 is a block diagram illustrating a system for generating appliances in accordance with methods and processes of the present invention.

FIG. 25 is a simplified block diagram of a data processing system 2400 that may be used in executing methods and processes described herein. The data processing system 2400 typically includes at least one processor 2402 that communicates with a number of peripheral devices via bus subsystem 2404. These peripheral devices typically include a storage subsystem 2406 (memory subsystem 2408 and file storage subsystem 2414), a set of user interface input and output devices 2418, and an interface to outside networks 2416, including the public switched telephone network. This interface is shown schematically as "Modems and Network Interface" block 2416, and is coupled to corresponding interface devices in other data processing systems via communication network interface 2424. Data processing system 2400 can include, for example, one or more computers, such as a personal computer, workstation, mainframe, and the like.

The user interface input devices 2418 are not limited to any particular device, and can typically include, for example, a keyboard, pointing device, mouse, scanner, interactive displays, etc. Similarly, various user interface output devices can be employed in a system of the invention, and can include, for example, one or more of a printer, display (e.g., visual, non-visual) system/subsystem, controller, projection device, audio output, and the like.

Storage subsystem 2406 maintains the basic required programming, including computer readable media having instructions (e.g., operating instructions, etc.), and data constructs. The program modules discussed herein are typically stored in storage subsystem 2406. Storage subsystem 2406 typically comprises memory subsystem 2408 and file storage subsystem 2414. Memory subsystem 2408 typically includes a number of memories (e.g., RAM 2410, ROM 2412, etc.) including computer readable memory for storage of fixed instructions, instructions and data during program execution, basic input/output system, etc. File storage subsystem 2414 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the Internet's World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 2420 includes any means for obtaining an image of a patient's teeth (e.g., from casts 2421), some of which have been described herein above, which can be obtained either from the patient or from treating professional, such as an orthodontist, and includes means of providing the image data/information to data processing system 2400 for further processing. In some embodiments, scanner 2420 may be located at a location remote with respect to other components of the system and can communicate image data and/or information to data processing system 2400, for example, via a network interface 2424. Fabrication system 2422 fabricates dental appliances 2423 based on a treatment plan, including data set information received from data processing system 2400. Fabrication machine 2422 can, for example, be located at a remote location and receive data set information from data processing system 2400 via network interface 2424.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for detecting deviations from an orthodontic treatment plan, the system comprising:
   at least one processor; and
   a computer readable medium including instructions that when executed cause the at least one processor to:
      receive a tracking model comprising a digital representation of an actual arrangement of a patient's teeth after an orthodontic treatment plan has begun for the patient for comparison to a plan model comprising a pre-determined planned arrangement of the patient's teeth;
      perform an alignment between the plan model and the tracking model using a partial region beyond a tooth crown of the plan model and a partial region beyond a tooth crown of the tracking model such that stationary elements of each of the plan model and the tracking model are aligned with one another, the alignment including detecting the partial region of each of the tracking model and the plan model based on a polygon formed from predetermined points on at least some of the teeth in the plan model and a polygon formed from predetermined points on at least some of the teeth in the tracking model; and
      detect one or more positional differences between the actual arrangement of the patient's teeth and the pre-determined planned arrangement of the patient's teeth.

2. The system of claim 1, wherein the tracking model is created via scanning at least one of a) the patient's teeth, and b) an impression of the patient's teeth.

3. The system of claim 1, wherein the orthodontic treatment plan comprises a plurality of planned successive tooth arrangements for moving teeth along a treatment path from an initial arrangement to a selected final arrangement.

4. The system of claim 1, wherein the plan model comprises a previously segmented model of the patient's teeth and the tracking model comprises a non-segmented raw model of the patient's teeth and jaw in the actual arrangement.

5. The system of claim 1, wherein the performance of the alignment includes:
   calculating an alignment transform using the detected partial regions, and
   aligning the tracking model and the plan model using the calculated alignment transform.

6. The system of claim 1, wherein the partial regions include at least one of a gingiva shape, palatine rugae and hard plate.

7. The system of claim 1, wherein the detecting the partial region of each of the tracking model and the plan model includes, for each model:
   calculating a lingual cementoenamal junction (CEJ) point on each tooth in the model;
   connecting the cementoenamel junction (CEJ) points in sequence to form the respective polygon;
   filtering out faces which are outside of the respective polygon; and
   after filtering, forming the respective partial region by combining remaining faces.

8. A method for detecting deviations from an orthodontic treatment plan, the method comprising:
   receiving a tracking model comprising a digital representation of an actual arrangement of a patient's teeth after an orthodontic treatment plan has begun for the patient for comparison to a plurality of plan models, each plan model comprising a respective pre-determined planned arrangement of the patient's teeth;
   performing an alignment between each plan model and the tracking model using a partial region beyond a tooth crown of the respective plan model and a partial region beyond a tooth crown of the tracking model such that stationary elements of each of the respective plan model and the tracking model are aligned with one another, the alignment including detecting the partial region of each of the tracking model and the respective plan model based on a polygon formed from predetermined points on at least some of the teeth in the respective plan model and a polygon formed from predetermined points on at least some of the teeth in the tracking model;
   selecting one of the respective plan models in which the planned arrangement of the patient's teeth best matches the actual arrangement of the patient's teeth; and
   detecting one or more positional differences between the actual arrangement of the patient's teeth and the planned arrangement of the patient's teeth in the selected plan model.

9. The method of claim 8, wherein the tracking model is created via scanning at least one of: a) the patient's teeth, and b) an impression of the patient's teeth.

10. The method of claim 8, wherein the orthodontic treatment plan comprises a plurality of planned successive tooth arrangements for moving teeth along a treatment path from an initial arrangement to a selected final arrangement.

11. The method of claim 8, wherein each plan model comprises a previously segmented model of the patient's teeth and the tracking model comprises a non-segmented raw model of the patient's teeth and jaw in the actual arrangement.

12. The method of claim 8, comprising detecting one or more positional differences between the actual arrangement of the patient's teeth and each of the respective planned arrangements of the patient's teeth.

13. The method of claim 8, wherein said performing an alignment between each plan model and the tracking model includes:
   calculating an alignment transform using the detected partial regions, and
   aligning the tracking model and the respective plan model using the calculated alignment transform.

14. The method of claim 8, wherein the partial regions include at least one of a gingiva shape, palatine rugae and hard plate.

15. The method of claim 8, wherein said detecting the partial region of each of the tracking model and the plan model includes, for each model:
   calculating a lingual cementoenamal junction (CEJ) point on each tooth in the model;
   connecting the cementoenamel junction (CEJ) points in sequence to form the respective polygon;
   filtering out faces which are outside of the respective polygon; and
   after filtering, forming the respective partial region by combining remaining faces.

16. A system for detecting deviations from an orthodontic treatment plan, the system comprising:

at least one processor; and a computer readable medium including instructions that when executed cause the at least one processor to:

receive a tracking model comprising a digital representation of an actual arrangement of a patient's teeth after an orthodontic treatment plan has begun for the patient for comparison to a plurality of plan models, each plan model comprising a respective pre-determined planned arrangement of the patient's teeth;

perform an alignment between each plan model and the tracking model using a partial region beyond a tooth crown of the respective plan model and a partial region beyond a tooth crown of the tracking model such that stationary elements of each of the respective plan model and the tracking model are aligned with one another, the alignment including detecting the partial region of each of the tracking model and the respective plan model based on a polygon formed from predetermined points on at least some of the teeth in the respective plan model and a polygon formed from predetermined points on at least some of the teeth in the tracking model;

select one of the respective plan models in which the planned arrangement of the patient's teeth best matches the actual arrangement of the patient's teeth; and detect one or more positional differences between the actual arrangement of the patient's teeth and the planned arrangement of the patient's teeth in the selected plan model.

17. The system of claim 16, wherein the tracking model is created via scanning at least one of: a) the patient's teeth, and b) an impression of the patient's teeth.

18. The system of claim 16, wherein the orthodontic treatment plan comprises a plurality of planned successive tooth arrangements for moving teeth along a treatment path from an initial arrangement to a selected final arrangement.

19. The system of claim 16, wherein each respective plan model comprises a previously segmented model of the patient's teeth and the tracking model comprises a non-segmented raw model of the patient's teeth and jaw in the actual arrangement.

20. The system of claim 16, wherein the instructions, when executed, cause the at least one processor to detect one or more positional differences between the actual arrangement of the patient's teeth and the planned arrangement of the patient's teeth for each of the respective plan models.

21. The system of claim 16, wherein the instructions, when executed, cause the at least one processor to:

calculate an alignment transform using the detected partial regions, and align the tracking model and the respective plan model using the calculated alignment transform.

22. The system of claim 16, wherein the partial regions include at least one of a gingiva shape, palatine rugae and hard plate.

23. The system of claim 16, wherein the instructions, when executed, cause the at least one processor to:

calculate a lingual cementoenamal junction (CEJ) point on each tooth in the model;

connect the cementoenamel junction (CEJ) points in sequence to form the respective polygon;

filter out faces which are outside of the respective polygon; and after said filtering, form the respective partial region by combining remaining faces.

* * * * *